(12) United States Patent
Alkhatib et al.

(10) Patent No.: US 7,909,844 B2
(45) Date of Patent: Mar. 22, 2011

(54) CATHETERS HAVING ACTUATABLE LUMEN ASSEMBLIES

(75) Inventors: Yousef Alkhatib, Maple Grove, MN (US); Matt Heidner, Maple Grove, MN (US); Tracee Eidenschink, Wayzata, MN (US); Angela Kornkven Volk, Rogers, MN (US); John Blix, Maple Grove, MN (US); Dominick Godin, Mound, MN (US); Derek Sutermeister, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1120 days.

(21) Appl. No.: 11/496,175

(22) Filed: Jul. 31, 2006

(65) Prior Publication Data

US 2008/0027377 A1      Jan. 31, 2008

(51) Int. Cl.
*A61M 29/00*   (2006.01)
*A61M 25/10*   (2006.01)
*A61M 25/14*   (2006.01)

(52) U.S. Cl. ...... 606/192; 606/191; 606/194; 604/99.01

(58) Field of Classification Search ............... 606/108, 606/191, 194; 604/96.01, 99.04
See application file for complete search history.

(56) References Cited

U.S. PATENT DOCUMENTS

| | | | |
|---|---|---|---|
| 4,921,483 A | 5/1990 | Wijay et al. | |
| 5,026,377 A | 6/1991 | Burton et al. | |
| 5,250,167 A | 10/1993 | Adolf et al. | 204/299 |
| 5,534,007 A | 7/1996 | St. Germain et al. | |
| 5,573,520 A | 11/1996 | Schwartz et al. | 604/282 |
| 5,752,935 A | 5/1998 | Robinson et al. | 604/97 |
| 5,755,685 A | 5/1998 | Andersen | 604/53 |
| 5,771,902 A | 6/1998 | Lee et al. | |
| 5,855,565 A | 1/1999 | Bar-Cohen et al. | 604/104 |
| 5,919,164 A | 7/1999 | Andersen | 604/102 |
| 5,941,871 A | 8/1999 | Adams et al. | 604/523 |
| 5,947,927 A | 9/1999 | Mertens | 604/96 |
| 6,109,852 A | 8/2000 | Shahinpoor et al. | 414/1 |
| 6,113,579 A | 9/2000 | Eidenschink et al. | |
| 6,117,296 A | 9/2000 | Thomson | 204/607 |
| 6,120,522 A | 9/2000 | Vrba et al. | |
| 6,123,718 A | 9/2000 | Tu et al. | |
| 6,249,076 B1 | 6/2001 | Madden et al. | 310/363 |

(Continued)

FOREIGN PATENT DOCUMENTS

EP        0371486       6/1990

(Continued)

OTHER PUBLICATIONS

D. Zhou et al., "Actuators for the Cochlear Implant," *Synthetic Metals* 135-136 (2003) 39-40.

(Continued)

*Primary Examiner* — Anhtuan T Nguyen
*Assistant Examiner* — Sarah Webb
(74) *Attorney, Agent, or Firm* — Vidas, Arrett & Steinkraus P.A.

(57) ABSTRACT

A catheter comprises a first catheter shaft comprising a wall. The wall comprises at least one section of electroactive polymer having an actuated state and a non-actuated state and defines a first lumen. In the actuated state the first lumen has a first diameter and in the non-actuated state the first lumen has a second diameter, the first diameter being different than the second diameter.

4 Claims, 19 Drawing Sheets

U.S. PATENT DOCUMENTS

| | | | |
|---|---|---|---|
| 6,388,043 B1 | 5/2002 | Langer et al. | 528/80 |
| 6,514,237 B1 | 2/2003 | Maseda | 604/533 |
| 6,620,527 B2 | 9/2003 | Wang | |
| 6,626,934 B2 | 9/2003 | Blaeser et al. | |
| 6,679,836 B2 | 1/2004 | Couvillon, Jr. | 600/146 |
| 6,733,473 B1 | 5/2004 | Reifart et al. | 604/96.01 |
| 6,749,556 B2 | 6/2004 | Banik | 600/30 |
| 6,770,027 B2 | 8/2004 | Banik et al. | 600/146 |
| 6,790,221 B2 | 9/2004 | Monroe et al. | |
| 6,812,624 B1 | 11/2004 | Pei et al. | 310/800 |
| 6,835,173 B2 | 12/2004 | Couvillon, Jr. | 600/146 |
| 6,921,360 B2 | 7/2005 | Banik | 600/30 |
| 6,940,211 B2 | 9/2005 | Pelrine et al. | 310/330 |
| 6,969,395 B2 | 11/2005 | Eskuri | 606/200 |
| 6,982,514 B1 | 1/2006 | Lu et al. | 310/300 |
| 6,997,870 B2 | 2/2006 | Couvillon, Jr. | 600/146 |
| 7,063,761 B2 | 6/2006 | Couvillon, Jr. et al. | |
| 7,077,808 B2 | 7/2006 | Couvillon, Jr. | 600/466 |
| 7,744,619 B2 * | 6/2010 | Eidenschink | 606/194 |
| 2002/0052641 A1 | 5/2002 | Monroe et al. | |
| 2003/0068522 A1 | 4/2003 | Wang | 428/654 |
| 2003/0099684 A1 | 5/2003 | Domb | |
| 2003/0212306 A1 | 11/2003 | Banik | |
| 2003/0236445 A1 | 12/2003 | Couvillon, Jr. | 600/114 |
| 2004/0068161 A1 | 4/2004 | Couvillon, Jr. | 600/143 |
| 2004/0068220 A1 | 4/2004 | Couvillon, Jr. et al. | |
| 2004/0087982 A1 | 5/2004 | Eskuri | 606/153 |
| 2004/0138733 A1 | 7/2004 | Weber et al. | |
| 2004/0143160 A1 | 7/2004 | Couvillon, Jr. | 600/114 |
| 2005/0004425 A1 | 1/2005 | Banik | 600/30 |
| 2005/0085693 A1 | 4/2005 | Belson et al. | 600/146 |
| 2005/0102017 A1* | 5/2005 | Mattison | 623/1.11 |
| 2005/0107669 A1 | 5/2005 | Couvillon | 600/146 |
| 2005/0119213 A1 | 6/2005 | Klachigian | |
| 2005/0165439 A1* | 7/2005 | Weber et al. | 606/191 |
| 2005/0183259 A1 | 8/2005 | Eidenschink et al. | |
| 2005/0187536 A1 | 8/2005 | Shelso et al. | |
| 2006/0041264 A1 | 2/2006 | Eskuri | 606/153 |
| 2006/0111618 A1 | 5/2006 | Couvillon, Jr. | 600/152 |
| 2007/0142771 A1 | 6/2007 | Durcan | |

FOREIGN PATENT DOCUMENTS

| | | |
|---|---|---|
| WO | 9742412 A1 | 11/1997 |
| WO | 2004-014238 | 2/2004 |

OTHER PUBLICATIONS

E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir*, 14 (11), 2970-2975, 1998.

E.W.H. Jager, E. Smela, O. Inganas, "Microfabricating Conjugated Polymer Actuators," *Science*, 290, 1540-1545, 2000.

E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.

*Proceedings of the SPIE*, vol. 4329 (2001) entitled "Smart Structures and Materials" 2001. see Madden et al., "Polypyrrole actuators: modeling and performance," pp. 73-83.

U.S. Appl. No. 11/280,120, filed Nov. 16, 2005, Weber et al.

U.S. Appl. No. 11/368,927, filed Mar. 6, 2006, Kornkven Volk et al.

U.S. Appl. No. 11/411,360, filed Apr. 25, 2006, Kornkven Volk et al.

Non-Final Office Action mailed on Jan. 15, 2010 for U.S. Appl. No. 11/368,927.

Yoshioka et al., Epoxy-based Electroactive Polymer Gels, vol. 42, No. 4. pp. 404-408, Dec. 2002.

Electroactive Muscle/Materials Selection www.me.berkeley.edu/ME117/S05/finalproject/pdf/Electroactive_Muscle.pdf.

* cited by examiner

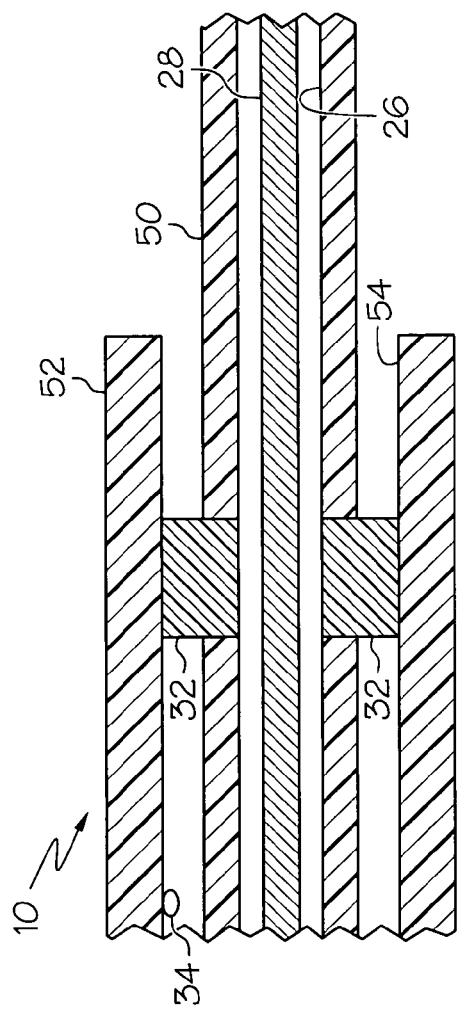
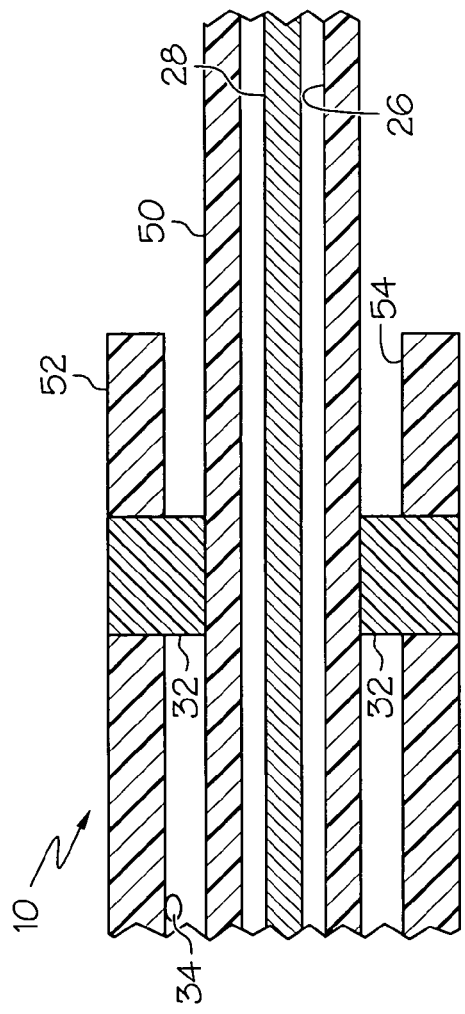

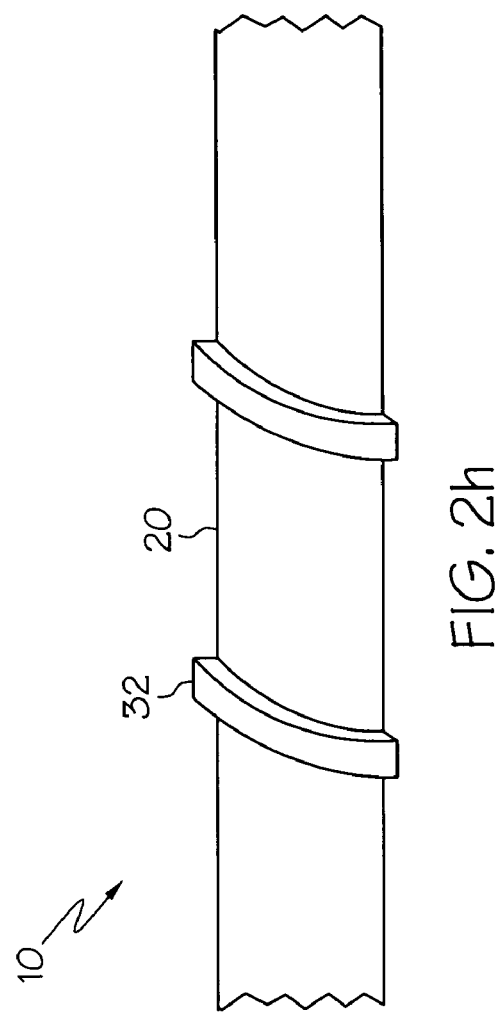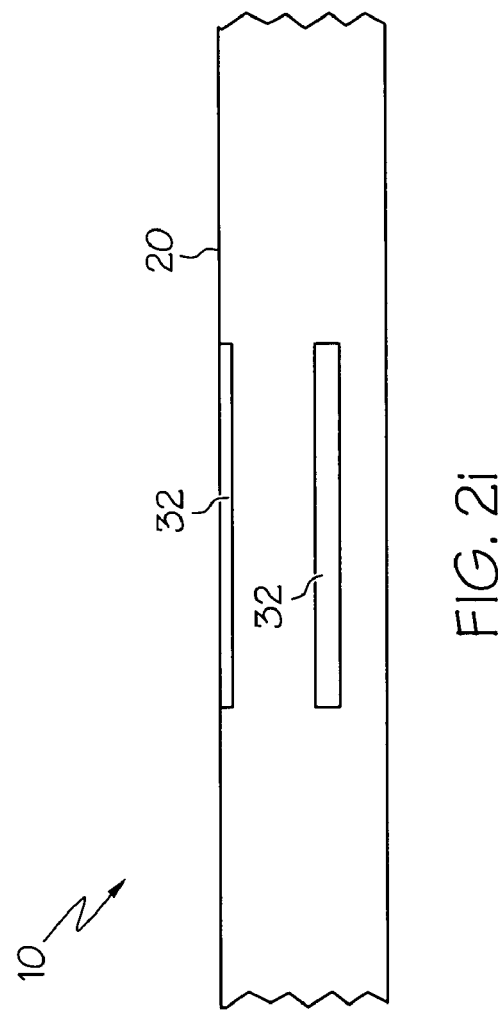

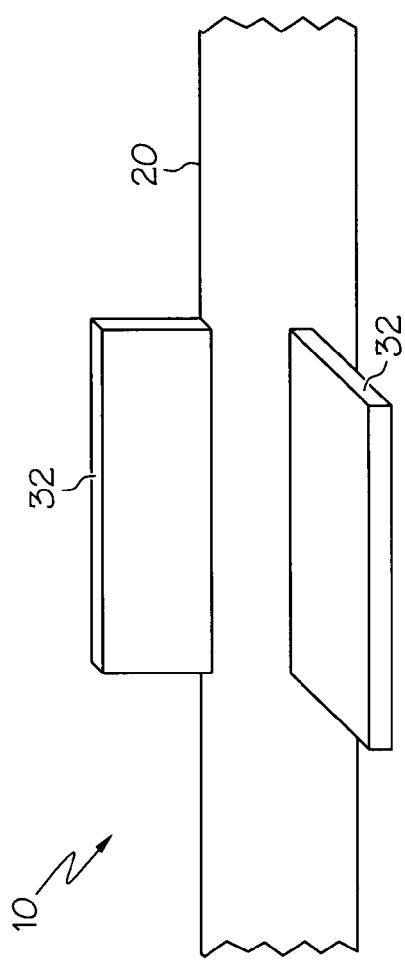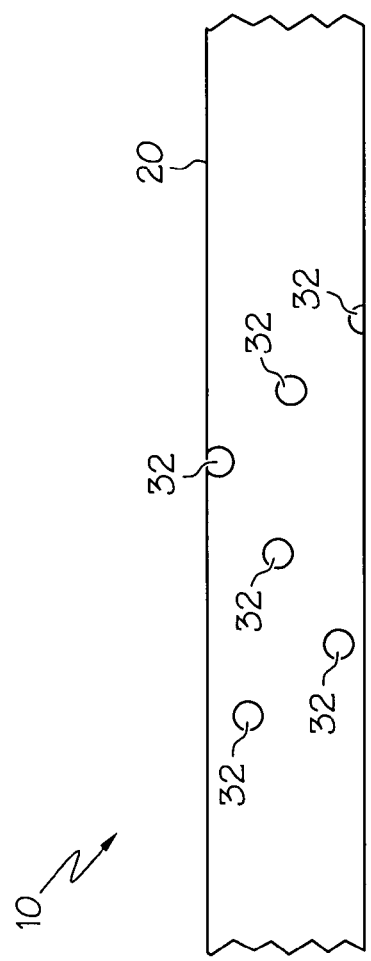

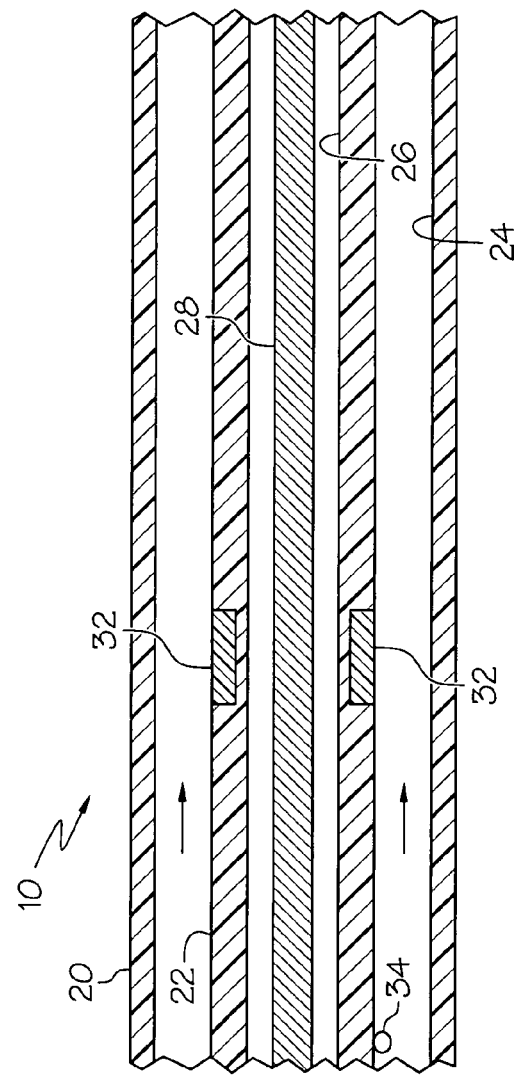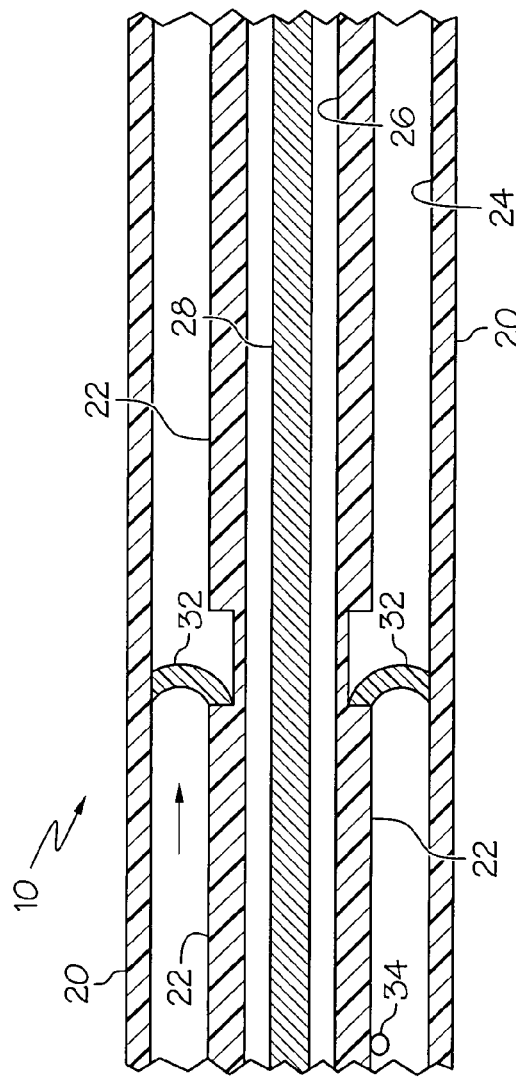

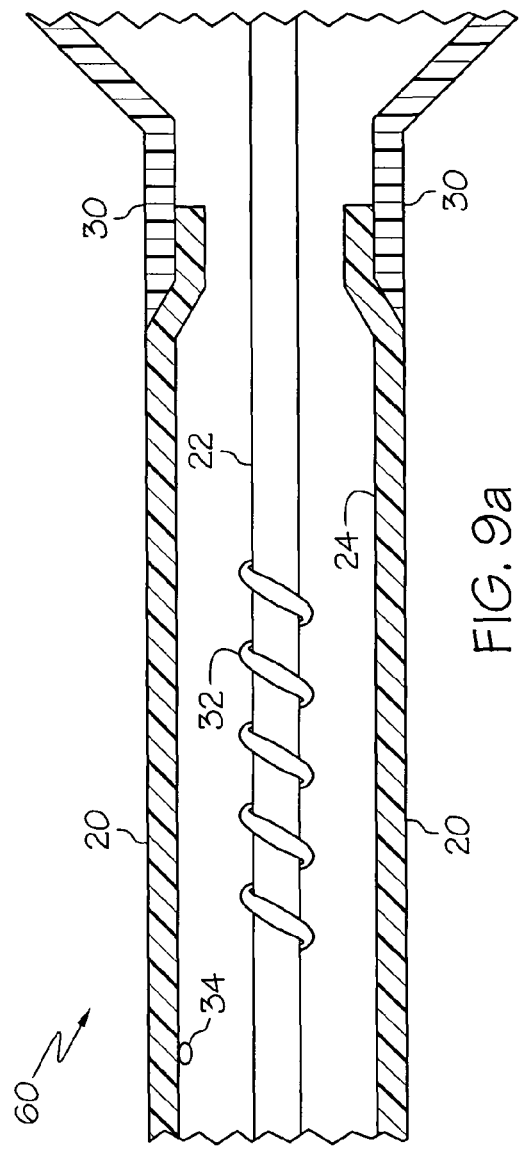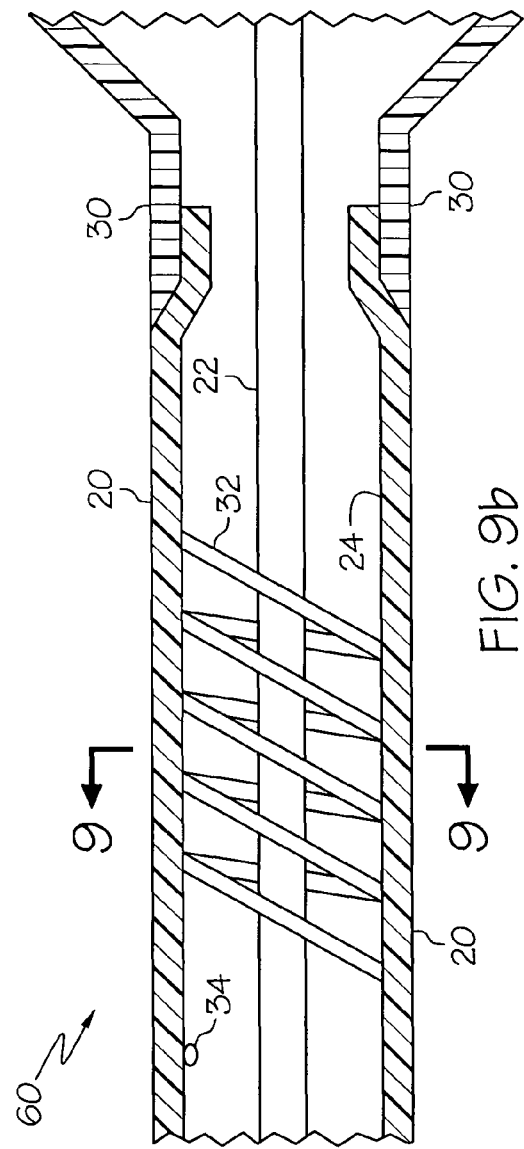

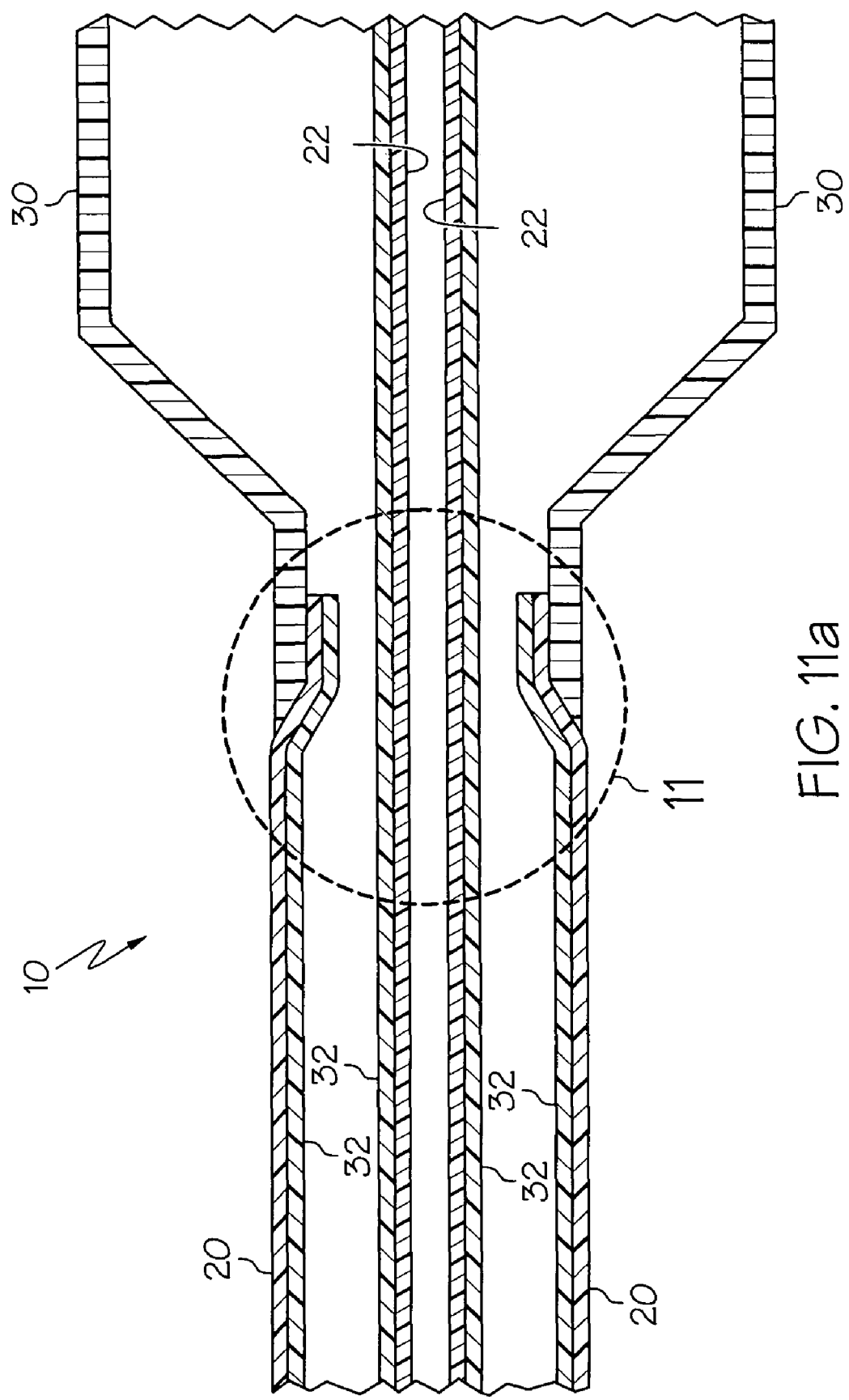

CATHETERS HAVING ACTUATABLE LUMEN ASSEMBLIES

CROSS-REFERENCE TO RELATED APPLICATIONS

Not Applicable

STATEMENT REGARDING FEDERALLY SPONSORED RESEARCH

Not Applicable

FIELD OF THE INVENTION

The present invention relates generally to intravascular catheters for performing medical procedures.

BACKGROUND OF THE INVENTION

Intravascular catheters are currently utilized in a wide variety of minimally-invasive or percutaneous medical procedures. Generally, an intravascular catheter enables a physician to remotely perform a medical procedure by inserting the catheter into the vascular system of the patient at an easily accessible location and navigating the tip of the catheter to a desirable target site. By this method, virtually any target site in the patient's vascular system may be remotely accessed.

Typically, a percutaneous procedure begins with the step of inserting a distal portion of the catheter into the patient's vasculature at a convenient location. Once the distal portion of the catheter has entered the patient's vascular system, the physician may urge the distal tip forward by applying forces to the proximal portion of the catheter. Typically, the path taken by a catheter through the vascular system is tortuous, requiring the catheter to change direction frequently. While advancing the catheter through the tortuous path of the patient's vasculature, the physician must steer the distal end of the catheter. During a percutaneous procedure, the physician typically is not able to manipulate the distal portion of the catheter directly. For this reason, physicians typically must steer the distal end of the catheter by applying torsional forces to the proximal portion of the catheter.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In one or more embodiments, the invention is directed to a catheter assembly such as a balloon catheter or other catheter having one or more lumens there through. In at least one embodiment, a catheter assembly comprises a first catheter shaft comprising a wall. The wall comprises at least one section of electroactive polymer having an actuated state and a non-actuated state and defines a first lumen. In the actuated state the first lumen haves a first diameter and in the non-actuated state the first lumen haves a second diameter, the first diameter being different than the second diameter.

These and other embodiments which characterize the invention are pointed out with particularity in the claims annexed hereto and forming a part hereof. However, for further understanding of the invention, the advantages and objectives obtained by its use, reference should be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 2d is a longitudinal cross-section view of a portion of a catheter engaged to the guide catheter because the section of EAP in the catheter is in an actuated state.

FIG. 2e is a longitudinal cross-section view of a portion of a guide catheter engaged to the catheter because the section of EAP in the guide catheter is in an actuated state.

FIG. 2h is the catheter shaft of FIG. 2g with the spiral section of EAP in an actuated state.

FIG. 2i is a side view of a catheter shaft with a plurality of longitudinal strips of EAP positioned about the circumference of the catheter shaft.

FIG. 2j is the catheter shaft of FIG. 2i with the longitudinal strips of EAP in an actuated state.

FIG. 2k is a side view of a catheter shaft with a plurality of spots of EAP about the circumference of the catheter shaft.

FIG. 2l is the catheter shaft of FIG. 2k with the spots of EAP in an actuated state.

FIGS. 6a and b is a longitudinal cross-section of an embodiment of the catheter showing the EAP in a non-actuated state (6a) and an actuated state (6b), where the EAP bends when actuated and blocks the inflation lumen.

Figure 7:
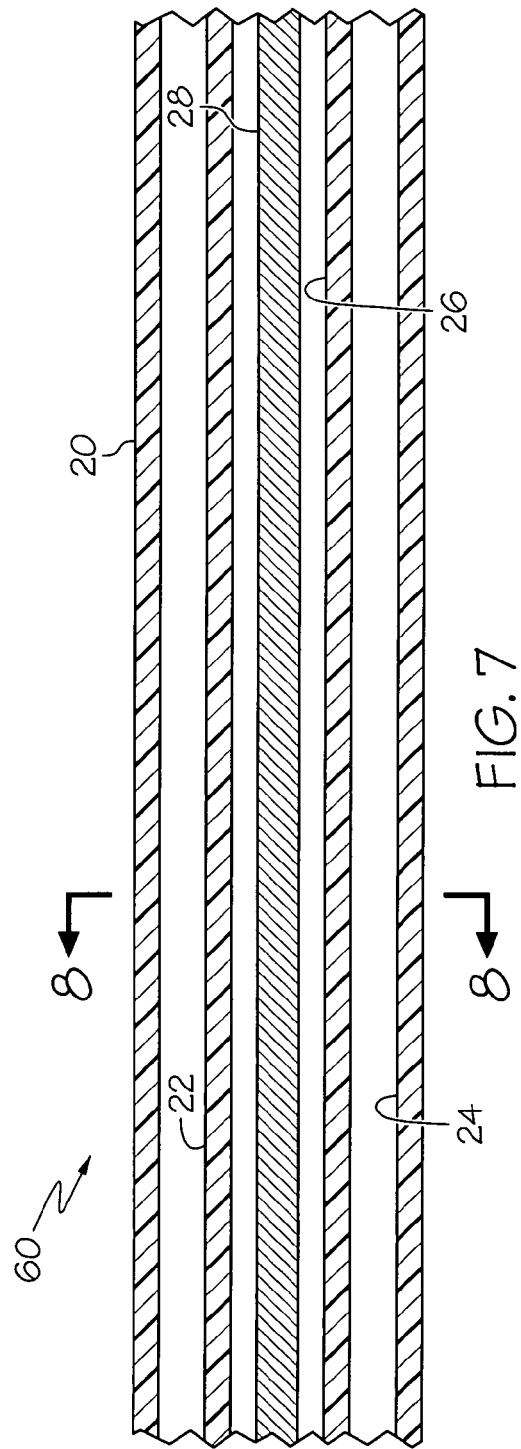

FIG. 7 is a longitudinal cross-section of a shaft of a generic balloon catheter.

Figure 8:
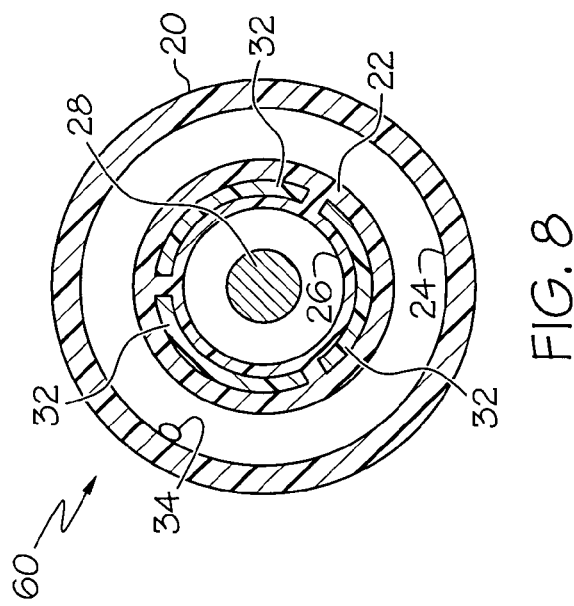

FIG. 8 is a cross-section view of the generic balloon catheter in FIG. 7 taken at line 10-10 where the generic balloon catheter is modified by an embodiment where the inner shaft of the catheter has three strips of EAP in a non-actuated state.

FIG. 9a is a longitudinal cross-section of a balloon catheter with a coil of EAP.

FIG. 9b is the balloon catheter of FIG. 9a with the coil of EAP in an actuated state.

Figure 9D:
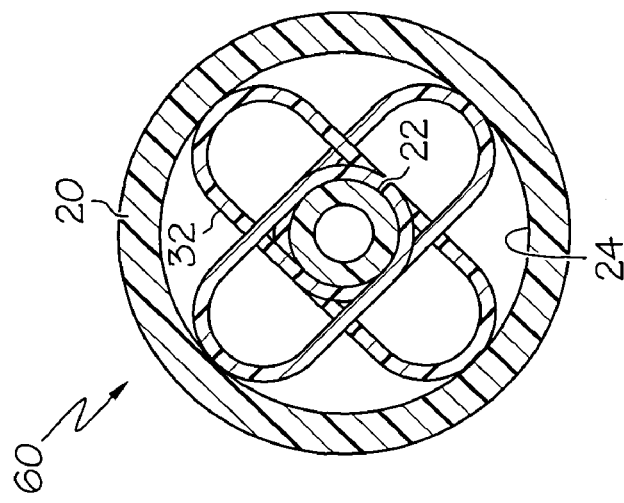
Figure 9C:
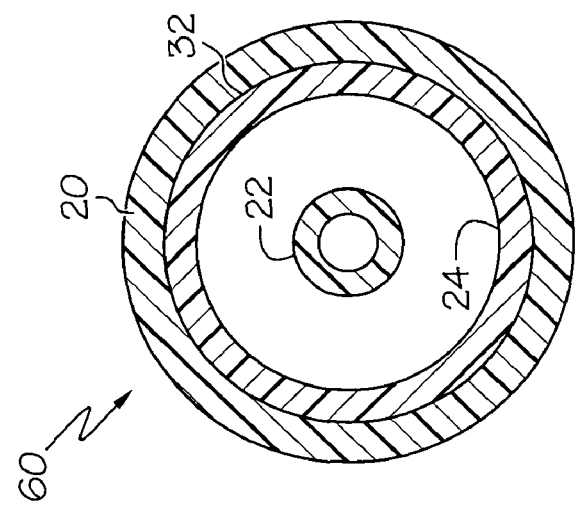

FIG. 9c is a cross section of the balloon catheter of FIG. 9b taken at line 9-9.

FIG. 9d is a cross-section of the balloon catheter of FIG. 9b taken at line 9-9, showing an alternative coil design.

Figure 10:
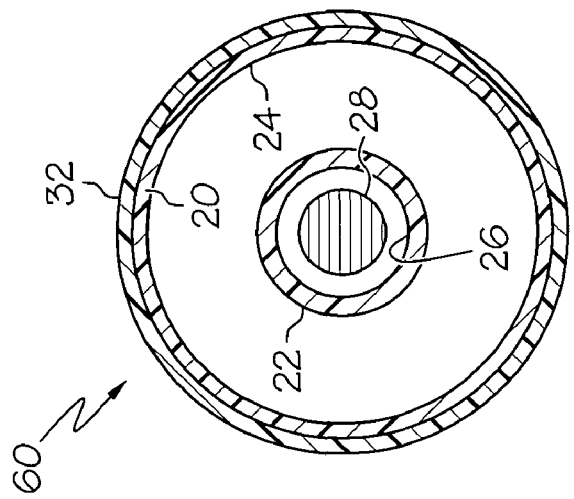

FIG. 10 is a cross-section of the generic balloon catheter in FIG. 7 along line 10-10 where the catheter is modified by the addition of EAP in a layer that forms the exterior surface of a portion of the outer shaft.

FIG. 11a is a longitudinal cross-section of a balloon catheter, the outer shaft wall having a layer of EAP on the interior surface, the inner shaft wall having a layer of EAP on the exterior surface.

Figure 11C:
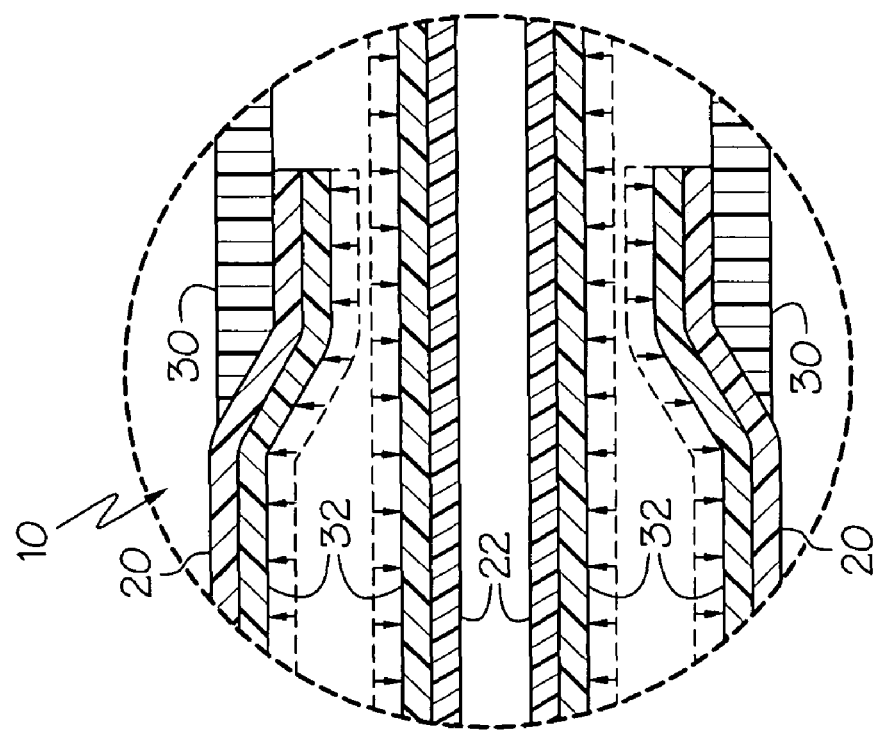
Figure 11B:
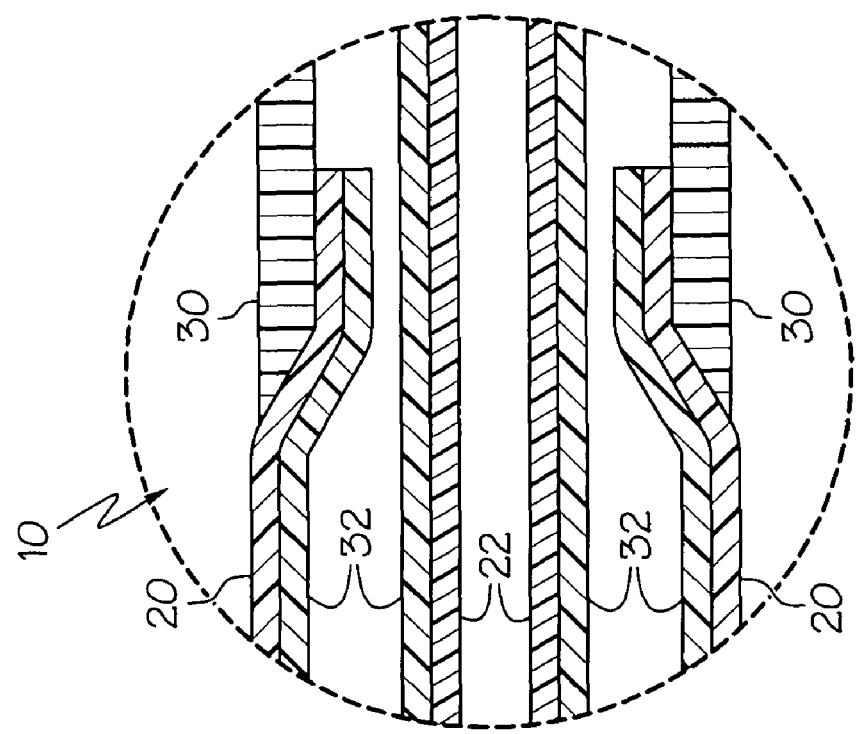

FIG. 11b is an enlarged view of a portion of the balloon catheter in FIG. 11a with the layers of EAP in a non-actuated state.

FIG. 11c is an enlarged view of a portion of the balloon catheter in FIG. 11a with the layer of EAP in an actuated state.

Figure 12A:
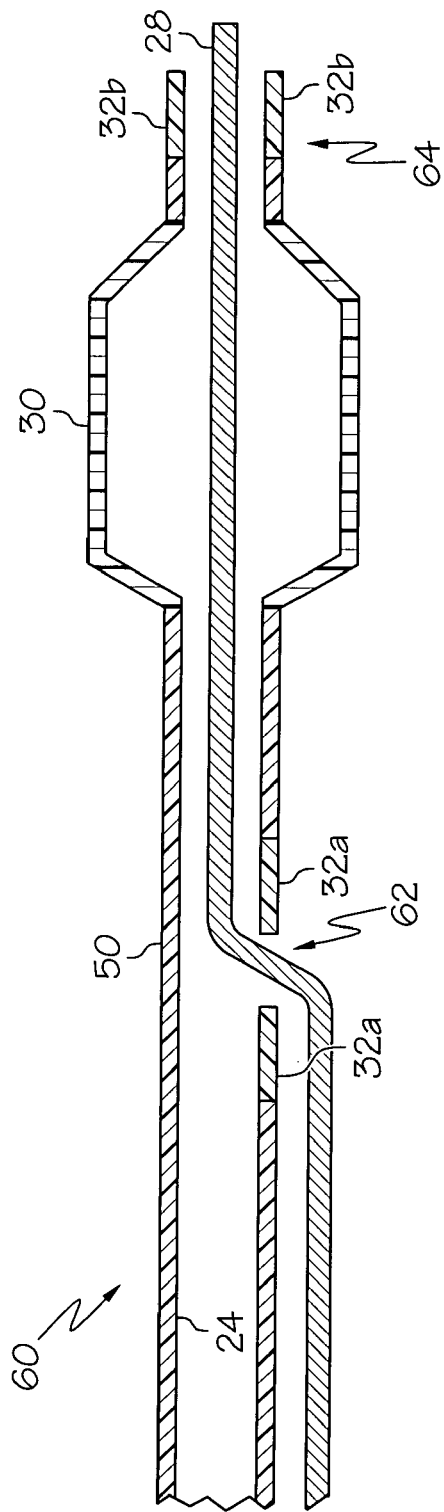

FIG. 12a is a longitudinal cross-section of a single lumen balloon catheter with sections of EAP in a non-actuated state.

Figure 12B:
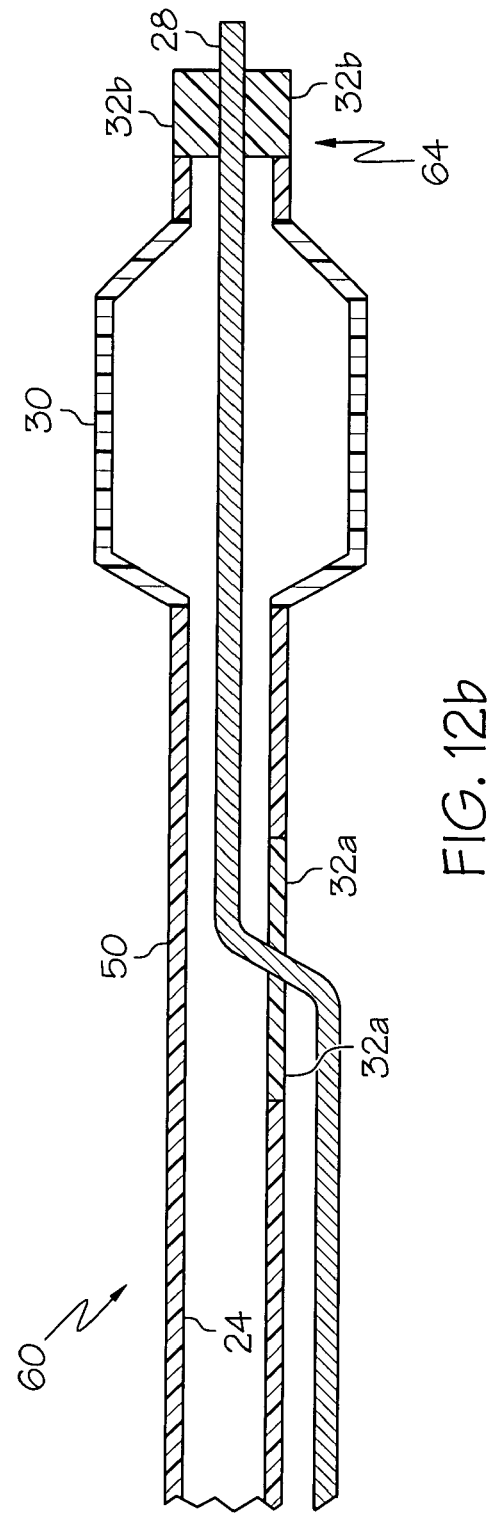

FIG. 12b is the balloon catheter of FIG. 12a with the sections of EAP in an actuated state.

Figure 12D:
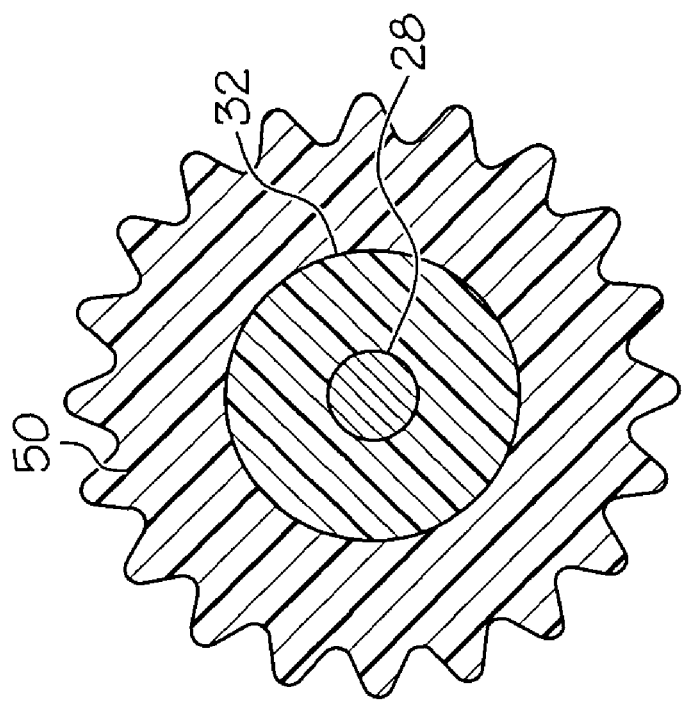
Figure 12C:
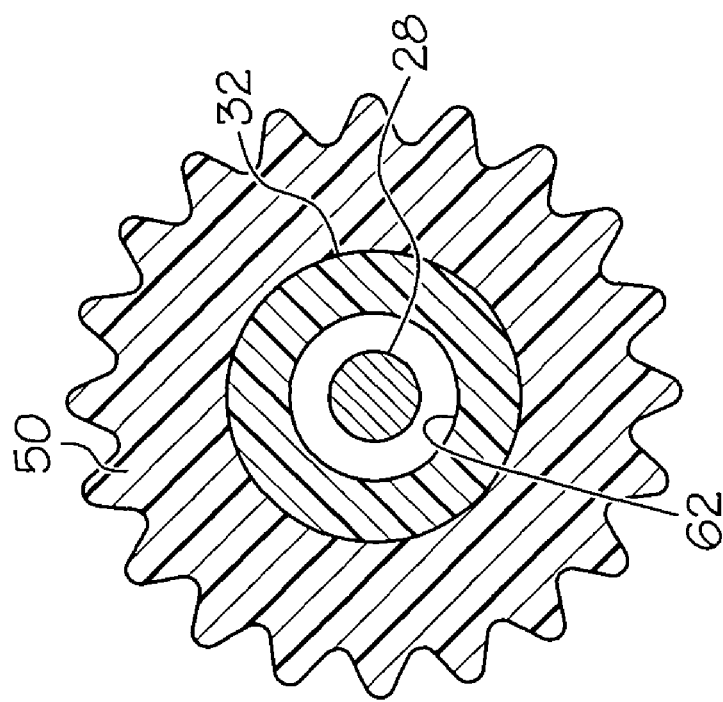

FIG. 12c is a side view of a portion of the balloon catheter showing the section of EAP, in a non-actuated state, surrounding the guide wire opening.

FIG. 12d is the side view of FIG. 12c with the section of EAP in an actuated state.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1C:
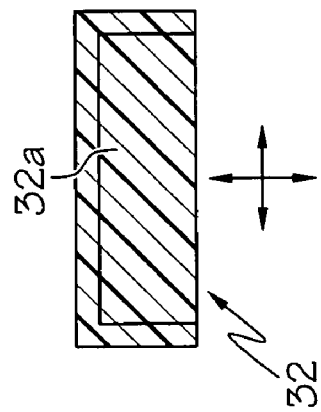
FIG. 1c depicts how EAP can increase or decrease from an initial size when actuated.
Figure 1B:
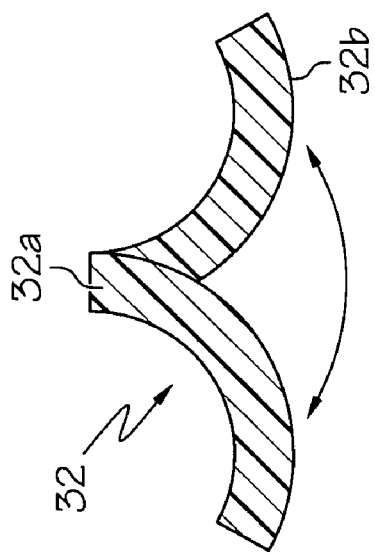
FIG. 1b depicts how EAP can bend when actuated.
Figure 1A:
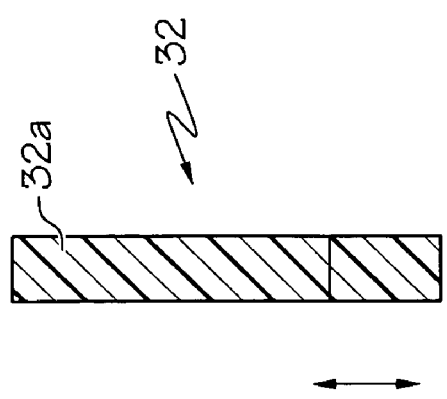
FIG. 1a depicts how EAP can increase or decrease from an initial length when actuated

FIGS. 1a-c depict different ways EAP 32 can behave when actuated. FIG. 1a depicts how EAP 32 can increase or decrease its linear length. When EAP 32a is actuated and the linear length is increased, it goes from an initial length of portion 32a to an actuated length of portion 32. When EAP 32 is actuated and the linear length is decreased, it goes from an initial length 32 to an actuated length of 32a. FIG. 1b shows how EAP 32 can bend when actuated with 32a denoting the EAP 32 prior to deformation and 32b denoting the EAP after deformation. Alternatively, EAP 32 can change from a straight configuration to a bent configuration or vice-versa upon actuation. FIG. 1c depicts how EAP 32 can increase or decrease its bulk or size, i.e. volumetrically expand or contract, when actuated. When EAP 32a is actuated and increases its bulk or size when actuated, it goes from an initial size of 32a to an actuated size of 32. When EAP 32 is actuated and decreases its bulk or size when actuated, it goes from an initial size of 32 to an actuated size of 32a.

EAP is used in a variety of inventive ways disclosed herein. It has been discovered that EAP can be of particular importance in the design of catheters. In particular, EAP may be used in catheters to selectively alter the cross-section or shape of a catheter, to serve as valves in catheters as well as in other ways discussed herein.

Figure 2A:
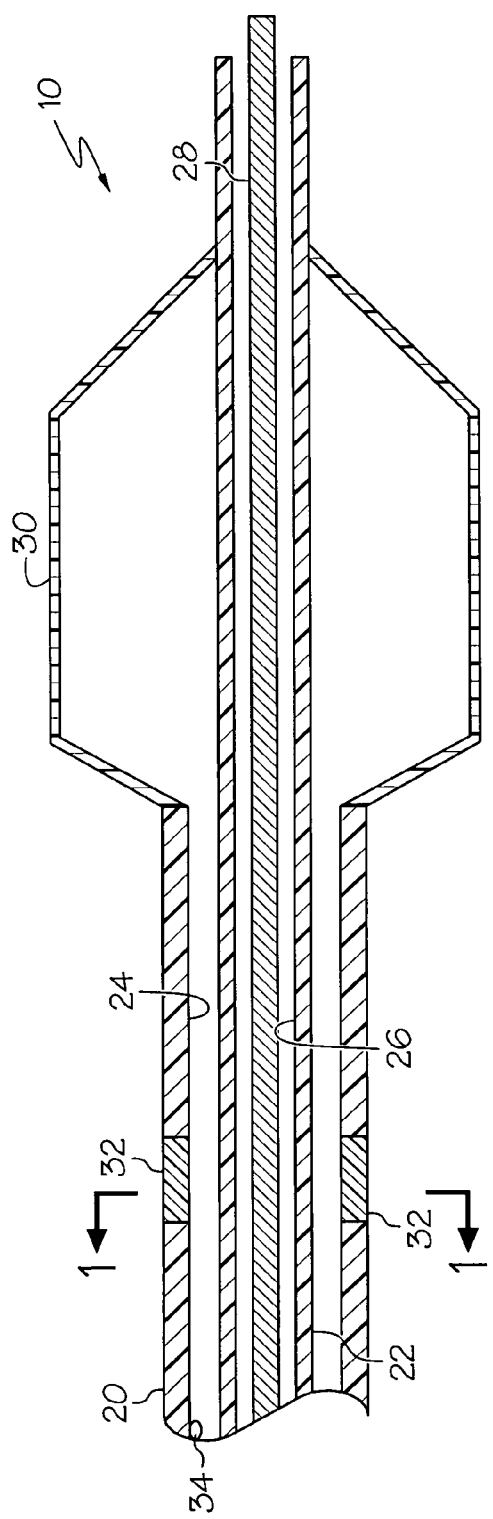
FIG. 2a is a longitudinal cross-section of an embodiment with the catheter having a balloon and an outer shaft with one section of EAP in a non-actuated state, the one section distal of EAP located proximal to the balloon.

In one embodiment of the invention, as shown in FIG. 2a, EAP 32 may be used to controllably alter the spatial configuration of a catheter shaft. FIG. 2a shows a longitudinal cross-section of an embodiment of the present invention. This embodiment can be used to anchor any device, such as catheter assembly 10, in place within the body lumen. Thus, the section or sections of EAP 32 can be used to engage a catheter with the vessel or a catheter with a guide catheter. The catheter assembly 10 has a balloon 30, an outer shaft 20, an inner shaft 22, and a guide wire 28. Both the walls of the outer shaft 20 and the inner shaft 22 have a thickness. The outer shaft 20 has an interior surface that defines an inflation lumen 24. The inner shaft 22 has an interior surface that defines a guide wire lumen 26. The outer shaft 20 of the catheter assembly 10 has one section of EAP 32. In this embodiment, the section of EAP 32 is circumferential, in the form of annular rings and FIG. 2 shows the EAP 32 in a non-actuated state For purposes of illustration only, the catheter assembly 10 is depicted in the majority of figures as a balloon catheter. However it can be appreciated that the catheter assembly 10 can be any one of multiple different intravascular or non-intravascular catheter types. A person of ordinary skill in the art will be familiar with different types of catheters appropriate for multiple embodiments. Some examples of other intravascular catheters include, but are not limited to, diagnostic catheters, guide catheters, atherectomy catheters, stent delivery catheters, and the like.

The figures also show an example of where the electrode 22 and counter electrode 24 may be placed. These are merely examples of possible positions for the electrode and counter electrode 24. As explained herein and in commonly assigned U.S. patent application Ser. No. 10/763,825, the entire content of which is incorporated by reference herein, the counter electrode 24 is placed so that at least a portion of the surface of the counter electrode 24 is generally in contact with the electrolyte to facilitate the actuation of the section of EAP 32.

Figure 2B:
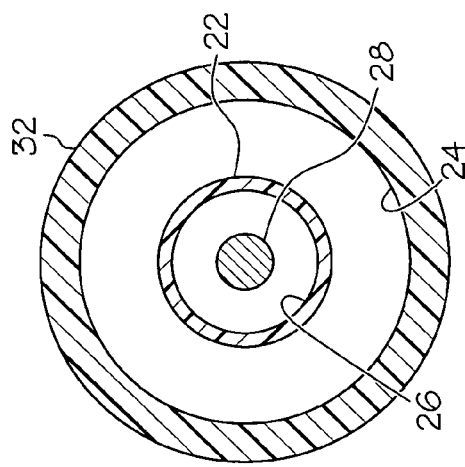
FIG. 2b is a cross-section view of the catheter in FIG. 2a at line 1-1.

FIG. 2b shows a cross-section of the catheter assembly 10 in FIG. 2a taken along line 1-1. In this embodiment, the band of EAP 32, in a non-actuated state, forms a section of wall of the outer shaft 20. Thus, the exterior surface of the section of EAP 32 is substantially flush with the exterior surface of the outer shaft 20. Similarly, the interior surface of the EAP 32 is substantially flush with the interior surface of the outer shaft 20. However, in some embodiments of the invention, the band of EAP 32 may form only a portion of the wall of the catheter shaft, i.e. the section of EAP 32 in a non-actuated state does not have the same thickness as the wall of the catheter shaft and is not flush with either the exterior surface or the interior surface of the shaft.

Figure 2C:
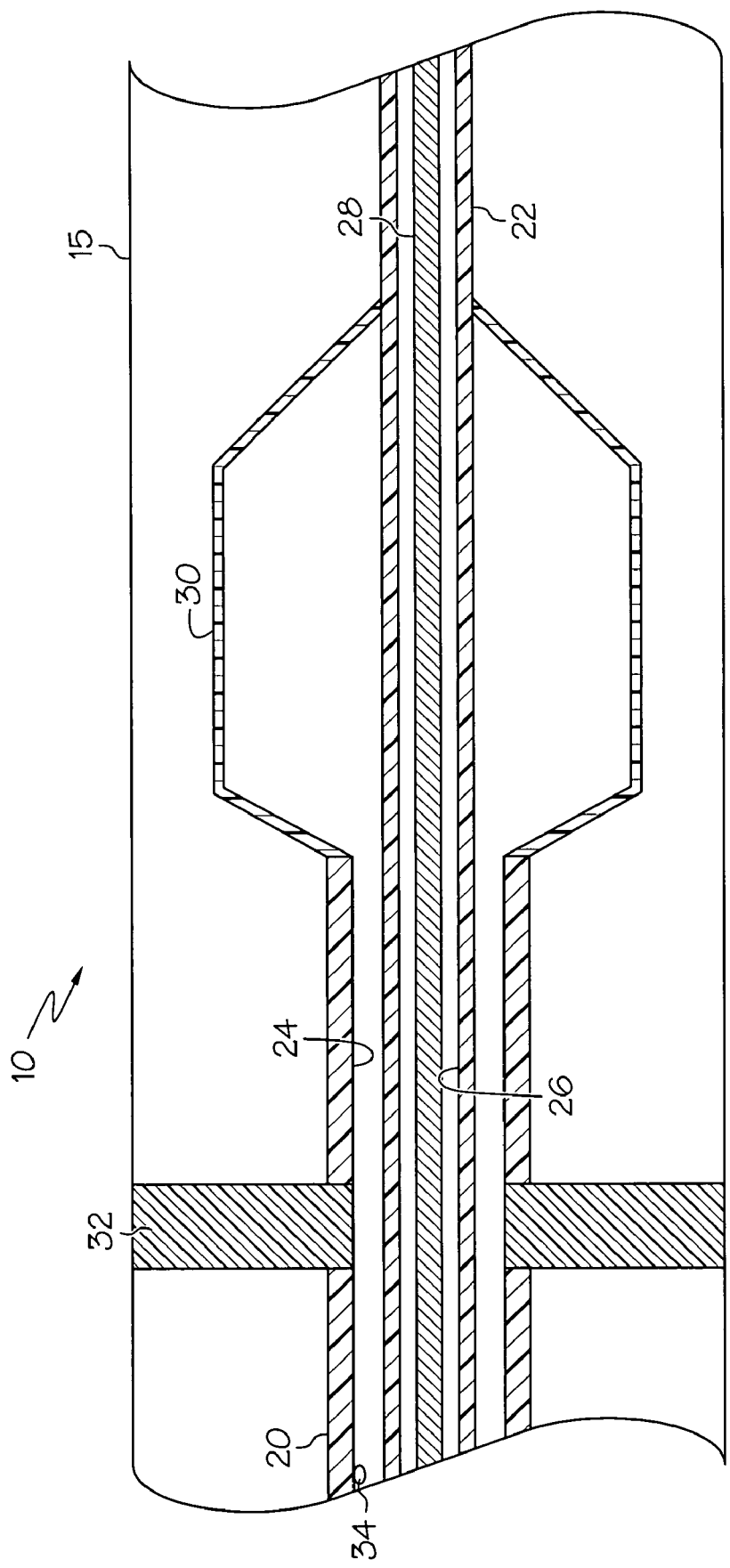
FIG. 2c is the longitudinal cross-section of the embodiment in FIG. 2a with the EAP in an actuated state.

FIG. 2c depicts how the catheter of FIG. 2a engages the vessel wall 15 when the sections of EAP 32 volumetrically expand in an actuated state. In this embodiment, the non-actuated thickness of the wall of the outer shaft 20 is smaller than the actuated thickness of the wall of the outer shaft 20, thus, the non-actuated outer diameter of the outer shaft 20 is smaller than the actuated diameter of the outer shaft 20. In addition, the non-actuated diameter of the catheter assembly 10 is smaller than the actuated diameter of the catheter assembly 10. When the section of EAP 32 is in an actuated state, the exterior surface of the section of EAP 32 is not substantially flush with the exterior surface of the outer shaft 20, while the interior surface of the section of EAP 32 is substantially flush with the interior surface of the outer shaft 20.

In one embodiment, shown in FIG. 2d, the catheter assembly 10 comprises a guide catheter 52 and a catheter 50 and the section of EAP 32 engages the outer surface of the catheter 50 to a guide catheter 52 when actuated. Thus, the guide catheter lumen 54 is occluded or the diameter of the guide catheter lumen 54 is reduced in size when the section of EAP 32 volumetrically expands when actuated. In this embodiment, the shaft of the catheter 50 has at least one section of EAP 32.

In at least one embodiment, the catheter 50 has a guide wire lumen 26 which contains a guide wire 28. The guide catheter 52 has a guide catheter lumen 54. When in an actuated state, the at least one section of EAP 32 volumetrically expands and engages the guide catheter 52. In this embodiment, the non-actuated thickness of the wall of the shaft of the catheter 50 is smaller than the actuated thickness of the wall of the shaft of the catheter 50, thus, the outer diameter of the shaft 50 is smaller in a non-actuated state than in an actuated state. In addition, the non-actuated diameter of the catheter assembly 10 is substantially the same as the actuated diameter of the catheter assembly 10.

Similar to the embodiment shown in FIGS. 2a-2b, the section of EAP 32, in a non-actuated state, forms a section of the shaft of the catheter 50. In a non-actuated state, the exterior surface of the section of EAP 32 is substantially flush with the exterior surface of the shaft of the catheter 50. Similarly, the interior surface of the section of EAP 32 is substantially flush with the interior surface of the catheter 50. However, the section of EAP 32 may form only a portion of the shaft of the catheter 50 and therefore may not be substantially flush with the exterior surface of the catheter 50.

In one embodiment, shown in FIG. 2e, the catheter assembly 10 comprises a guide catheter 52 and a catheter 50 and the guide catheter 52 has at least one section of EAP 32. As shown in FIG. 2e, when the section of EAP 32 is in an expanded state, the guide catheter 52 engages the catheter 50. In this embodiment, the catheter 50 has a guide wire lumen 26 which may contain a guide wire 28. The guide catheter 52 has a guide catheter lumen 54. In this embodiment, the non-actuated thickness of the wall of the shaft of the guide catheter 52 is smaller than the actuated thickness of the wall of the shaft of the guide catheter 52, thus, the inner diameter of the guide catheter 52 is smaller when in an actuated state than in a non-actuated state. In addition, the non-actuated diameter of the catheter assembly 10 is substantially the same as the actuated diameter of the catheter assembly 10.

Similar to the embodiment shown in FIGS. 2a-2b, the section of EAP 32, in a non-actuated state, forms a section of the shaft of the guide catheter 52. In a non-actuated state, the exterior surface of the section of EAP 32 is substantially flush with the exterior surface of the shaft of the guide catheter 52. Similarly, the interior surface of the section of EAP 32 in a non-actuated state is substantially flush with the interior surface of the shaft of the guide catheter 52. However, the section of EAP 32 in a non-actuated state may form only a portion of the shaft of the guide catheter 52 and therefore may not be substantially flush with the exterior surface of the shaft of the guide catheter 52. Although this embodiment shows only one section of EAP 32, it is within the scope of the invention to have a plurality of sections of EAP 32 in the shaft of the guide catheter 52.

Figure 2F:
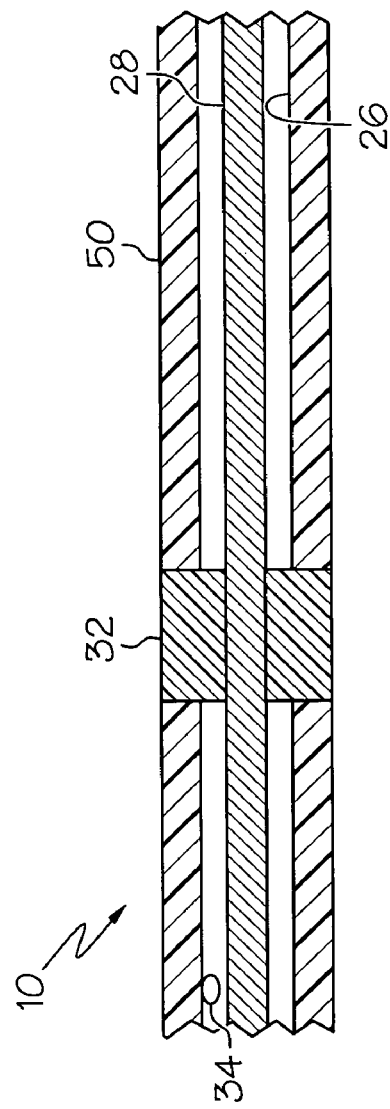
FIG. 2f is a longitudinal cross-section view of a portion of a catheter engaged to the guide wire because the section of EAP in the catheter is in an actuated state.

In one embodiment, shown in FIG. 2f, the section of EAP 32 engages the guide wire 28 when actuated. In this embodiment, the shaft of the catheter 50 has at least one section of EAP 32. The catheter 50 also has a guide wire lumen 26 which may contain a guide wire 28. When in an actuated state, the at least one section of EAP 32 volumetrically expands and engages the guide wire 28. In this embodiment, the non-actuated thickness of the wall of the shaft of the catheter 50 is smaller than the actuated thickness of the wall of the shaft of the catheter 50. Thus, the inner diameter of the catheter 50 or the diameter of the guide wire lumen 26 is smaller in an actuated state than in a non-actuated state. In addition, the non-actuated outer diameter of the catheter assembly 10 is substantially the same as the actuated outer diameter of the catheter assembly 10. Desirably, in use, this embodiment provides better push for the catheter and may help prevent the catheter from moving during deployment of a medical device.

Similar to the embodiment shown in FIGS. 2a-2b, the section of EAP 32, in a non-actuated state, forms a section of the shaft of the catheter 50. In a non-actuated state, the exterior surface of the section of EAP 32 is substantially flush with the exterior surface of the shaft of the catheter 50. Similarly, the interior surface of the section of EAP 32 is substantially flush with the interior surface of the shaft of the catheter 50. However, the section of EAP 32 may form only a portion of the shaft of the catheter 50 and therefore may not be substantially flush with the exterior surface of the catheter 50. Although this embodiment shows only one section of EAP 32, it is within the scope of the invention to have a plurality of sections of EAP 32 in the shaft of the catheter 50.

Figure 2G:
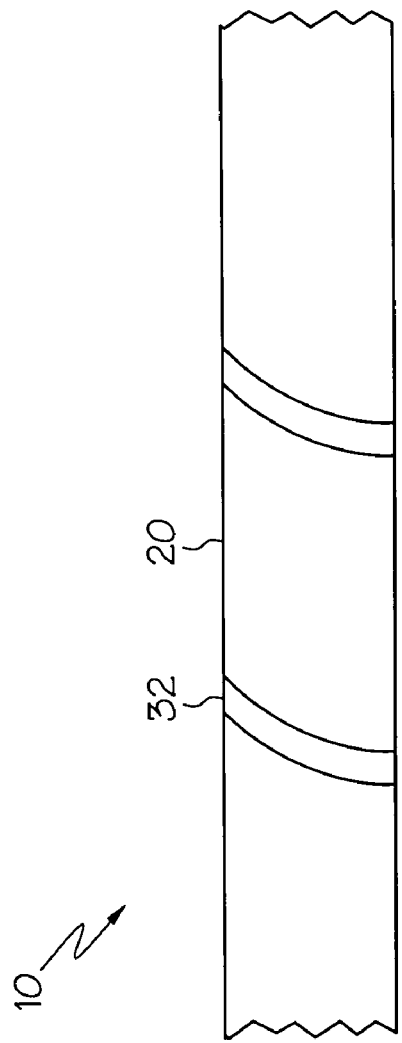
FIG. 2g is a side view of a catheter shaft with a spiral section of EAP.
Figure 21:
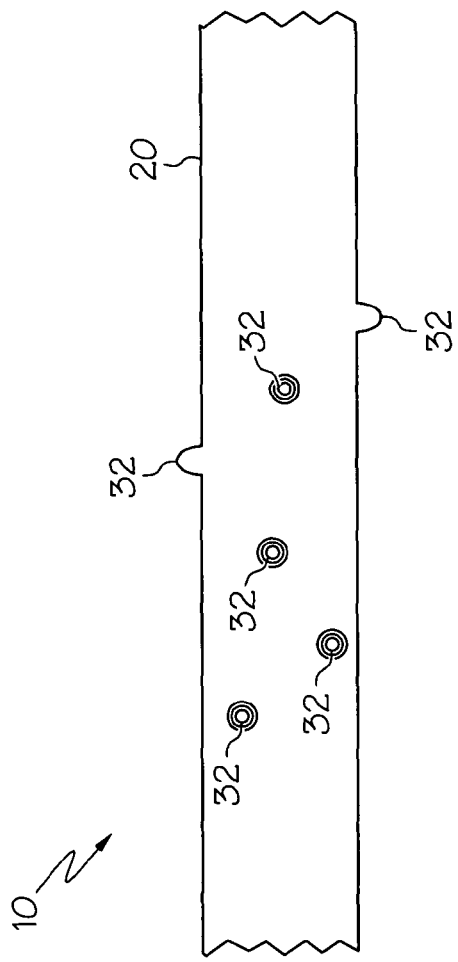

It is within the scope of the invention for the section or sections of EAP 32 to have any shape, for example but not limited to annular rings (as shown in FIG. 2a), spots, longitudinal strips, or spiral strips. The section(s) of EAP 32 may form a part of the wall of the outer shaft 20 or the section(s) of EAP 32 may be engaged to the exterior surface of the outer shaft 20. FIGS. 2g and 2h show an embodiment where the outer shaft 20 of the catheter assembly 10 has a section of EAP 32 in the form of a spiral strip. As shown in FIG. 2h, when the EAP 32 is in an expanded state, a spiral wall of EAP 32 is formed. This engages the catheter assembly 10 to either the vessel wall or to a guide catheter. Thus, the outer diameter of the catheter assembly 10 is larger in an actuated state than in a non-actuated state.

FIGS. 2i and 2j depict an embodiment where the outer shaft 20 of the catheter assembly 10 has a plurality of sections of EAP 32 which are in the form of longitudinal strips positioned about the circumference of the outer shaft 20. The sections of EAP 32 volumetrically expand when in an actuated state to form longitudinal walls, as shown in FIG. 2j. Thus, the outer diameter of the catheter assembly 10 is larger in an actuated state than in a non-actuated state. In use, this embodiment does not stop the flow of blood or other fluids when the EAP 32 is in an actuated state because fluids can still pass between the outer shaft 20 and the blood vessel, FIGS. 2k and 2l depict an embodiment where the outer shaft 20 has a plurality of sections of EAP 32 which are in the form of spots positioned about the circumference of the outer shaft 20. The spots of EAP 32 can have any shape, for example, but not limited to, circular, diamond, star-shape, rectangular, or square. Each spot of EAP 32 volumetrically expands in an expanded state, as shown in FIG. 2*l*. In this embodiment, a bump or hump is formed when the EAP 32 is in an expanded state. In one embodiment, the entire spot of EAP 32 volumetrically expands to the same height forming a pillar. Thus, the outer diameter of the catheter assembly 10 is larger in an actuated state than in a non-actuated state due to the actuation of the section of EAP 32. In use, these embodiments do not stop the flow of blood or other fluids when the section of EAP 32 is in an actuated state because fluids can still pass between the outer shaft 20 and the blood vessel.

The number and placement of the sections of EAP 32 can be varied. In at least one embodiment, the catheter shaft 50 has a plurality of circumferential bands of EAP 32. In at least one embodiment, there are a plurality of circumferential bands positioned along the shaft 50 at discrete longitudinal locations. It is also within the scope of the invention to have three, four, five, six, seven, or more circumferential bands of EAP 32.

Figure 3A:
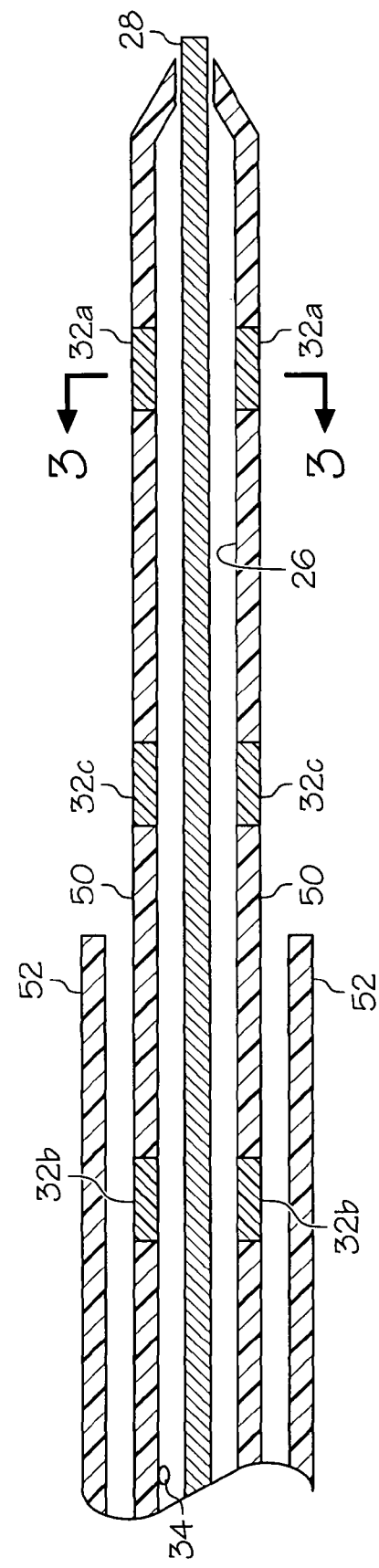
FIG. 3a is a longitudinal cross-section view of an embodiment with a catheter assembly comprising a guide catheter and a catheter with two circumferential bands of EAP, one band of EAP located at the distal end region and one circumferential band of EAP located proximal to the distal band of EAP.
Figure 3C:
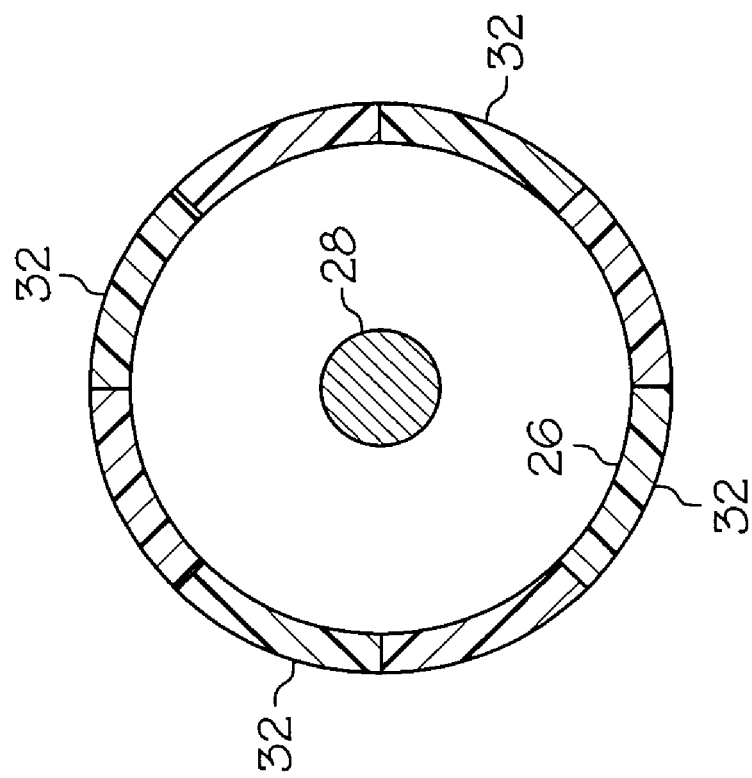
FIG. 3c is a cross section of the catheter in FIG. 3a taken at line 3-3 showing an embodiment where there are a plurality of sections of EAP at that longitudinal position.
Figure 3B:
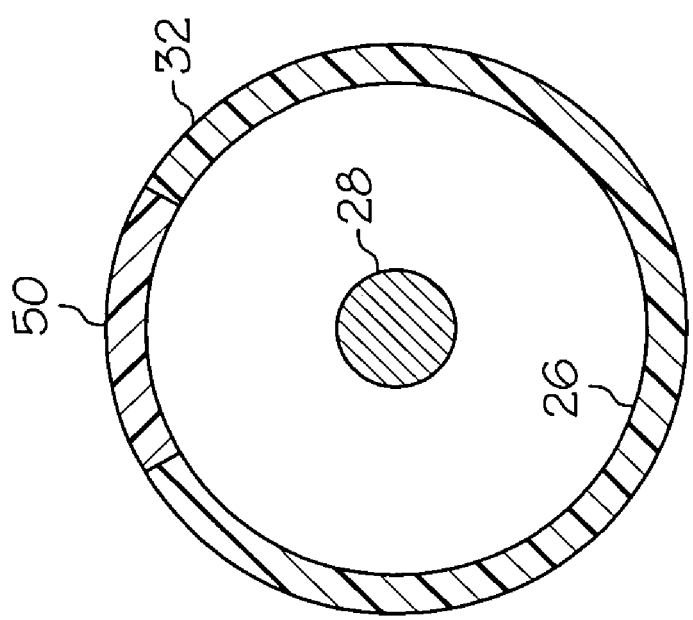
FIG. 3b is a cross section of the catheter in FIG. 3a taken at line 3-3, showing an embodiment where the EAP is an incompletely circumferential band.
Figure 3D:
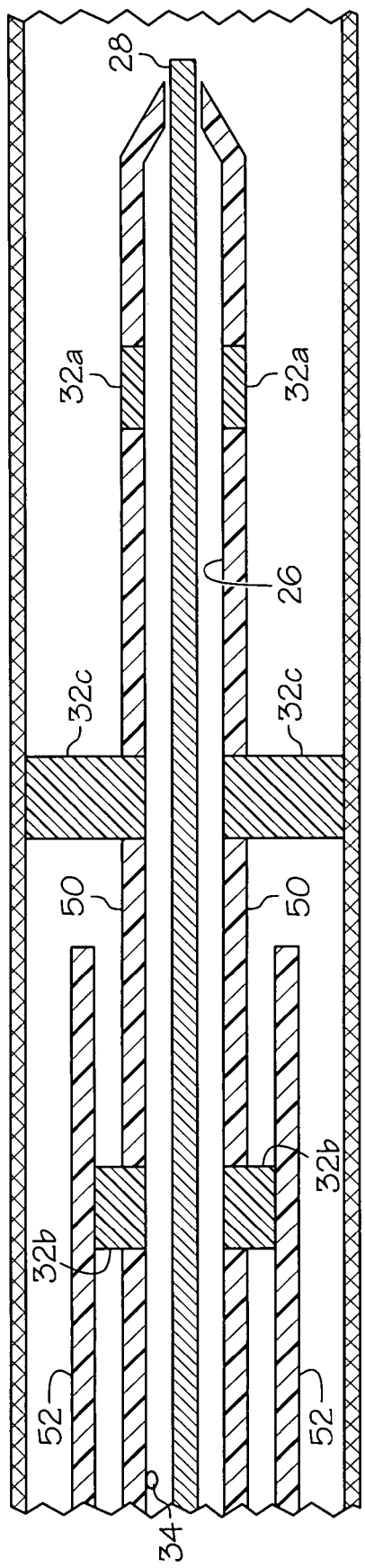
FIG. 3d is the catheter assembly of FIG. 3a within a blood vessel with two of the circumferential bands of EAP in an actuated state.

FIGS. 3*a* and 3*d* show an embodiment of a catheter assembly comprising a guide catheter 52 and a catheter shaft 50 with three circumferential bands of EAP 32. The first circumferential band of EAP 32*a* is located at the distal end region of the catheter shaft 50, a second circumferential band of EAP 32*b* is located proximal to the distal bands of EAP 32*a* and 32*c* and a third circumferential band 32*c* is located proximal to the first band of EAP 32*a* and distal to the second band of EAP 32*b*. FIG. 3*d* illustrates how the catheter assembly would appear when in use within the blood vessel and two of the three circumferential bands of EAP 32 *b,c* are in an actuated state. In use, when the proximal circumferential band of EAP 32*b* is actuated it engages the interior of the guide catheter 52 or the vasculature. Thus, the guide catheter lumen 54 is occluded by the proximal circumferential band of EAP 32*b*, i.e. the diameter of the guide catheter lumen 54 is equal to zero. In use, when bands of EAP 32*a* and 32*c* are actuated, each band of EAP 32*a,c* engage the vasculature. In use, the third band of EAP 32*c* may or may not be actuated depending upon the occlusion. Note that in FIG. 3*d*, the third band of EAP 32*c* is in an actuated state and the distal band of EAP 32*a* is in a non-actuated state. Either one or both circumferential bands of EAP 32*a,c* may be actuated depending on how much and where the extra stabilization of the catheter assembly is required. In this embodiment, the non-actuated thickness of the wall of the shaft of the catheter 50 is smaller than the actuated thickness of the wall of the shaft of the catheter 50, thus the outer diameter of the catheter 50 is larger in an actuated state than in a non-actuated state, This embodiment can be used when the physician encounters an occlusion that is particularly hard to get the guide wire through because the bands of EAP 32 can be actuated in order to secure the catheter in the vasculature and allow more force to be applied to the guide wire so that it can traverse through the occlusion. In at least one embodiment, the catheter shaft has two circumferential bands of EAP 32, the first circumferential band, 32*a* and the second circumferential band, 32*b*.

In one embodiment, the sections of EAP 32*b* and 32*c* are incomplete circumferential bands, as shown in FIG. 3*b* which is a cross-section of the catheter assembly of FIG. 3*a* taken at line 3-3. This embodiment allows the catheter assembly to be secured within the vasculature yet the bands of EAP 32 do not completely block the flow of bodily fluids past the catheter assembly when the EAP 32 is in an actuated state.

In one embodiment, instead of two circumferential bands of EAP 32*b* and 32*c*, the sections of EAP 32*b* and 32*c*, are comprised of a plurality of sections of EAP 32 positioned circumferentially around the catheter shaft. This embodiment is shown in FIG. 3*c* which is a cross-section of the catheter assembly of FIG. 3*a* taken at line 3-3. The embodiment shown has four sections of EAP 32 positioned about the circumference of the catheter 50. However, there may be two, three, five, six, seven or eight sections of EAP 32 positioned about the circumference of the catheter shaft so long as the number and size of the sections of EAP 32 are sufficient to engage the catheter 50 with the vasculature yet fulfill the objective of allowing fluid to pass between the catheter assembly and the vasculature. Because there are spaces between the circumferentially positioned sections of EAP 32, the flow of bodily fluids is not blocked when the EAP 32 is in an actuated state.

Figure 4:
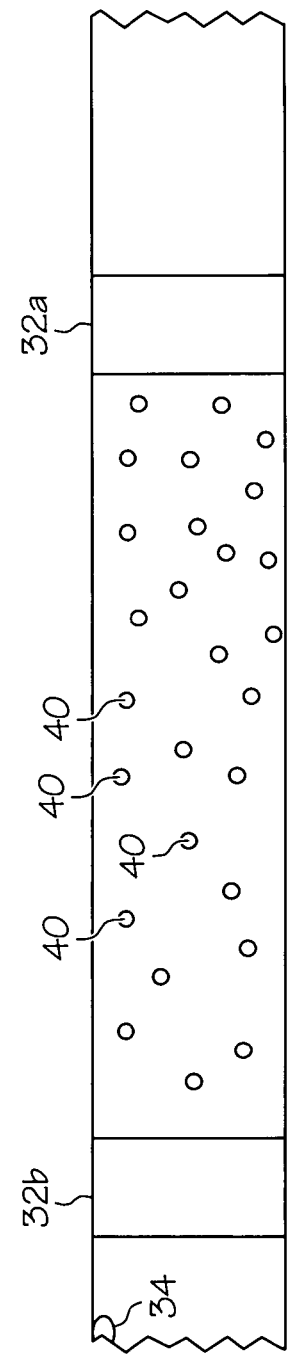
FIG. 4 is a perspective view of a catheter shaft with two circumferential sections of EAP which are longitudinally separated, the catheter shaft having a plurality of perforations in the area between the two circumferential sections of EAP.

FIG. 4 shows an embodiment of a catheter assembly 10 with two sections of EAP 32*a,b*. The catheter assembly 10 in this embodiment is not a balloon catheter. The shaft of the catheter assembly 10 has a lumen. The shaft of the catheter assembly 10 has two sections of EAP 32*a,b* which form circumferential bands. In this embodiment, the two circumferential bands of EAP 32*a,b* form a section of the wall of the catheter shaft. Thus, in an non-actuated state, the exterior surfaces of the bands of EAP 32*a,b* are substantially flush with the exterior surface of the shaft. In this embodiment, the non-actuated thickness of the shaft of the catheter is smaller than the actuated thickness of the shaft of the catheter, and the non-actuated diameter of the catheter assembly 10 is smaller than the actuated diameter of the catheter assembly 10. The two circumferential sections of EAP 32*a,b* are longitudinally separated by a section of the catheter shaft that has a plurality of perforations. The length of separation between the two sections of EAP 32*a,b* can be varied from around 0.1 mm to around 25 cm in order to provide catheters that have different treatment areas. When the two sections of EAP 32*a,b* are in an actuated state, they expand, engage the vessel wall and prevent bodily fluids from flowing between the catheter assembly and the vasculature. After the two sections of EAP 32*a,b* are in an actuated state, a beneficial agent can travel through the lumen of the catheter and exit through the perforations into the area of the vessel blocked by the two sections of EAP 32 *a,b*. The perforations may have any shape, including but not limited to circular, square, rectangular, triangular octogonal.

In another embodiment of the invention (not shown), the outer shaft 20 has only one section of EAP 32 positioned proximal to the balloon 30. In this embodiment, the EAP 32 volumetrically contracts when in an actuated state. Therefore, the exterior surface of the section of EAP 32, in a non-actuated state, is not substantially flush with the exterior surface of the outer shaft 20, but when the section of EAP 32 is in an actuated state, the exterior surface of the section of EAP 32 is substantially flush with the exterior surface of the outer shaft 20. Thus, in this embodiment, the non-actuated outer diameter of the outer shaft is larger than the actuated outer diameter of the outer shaft.

Figure 5:
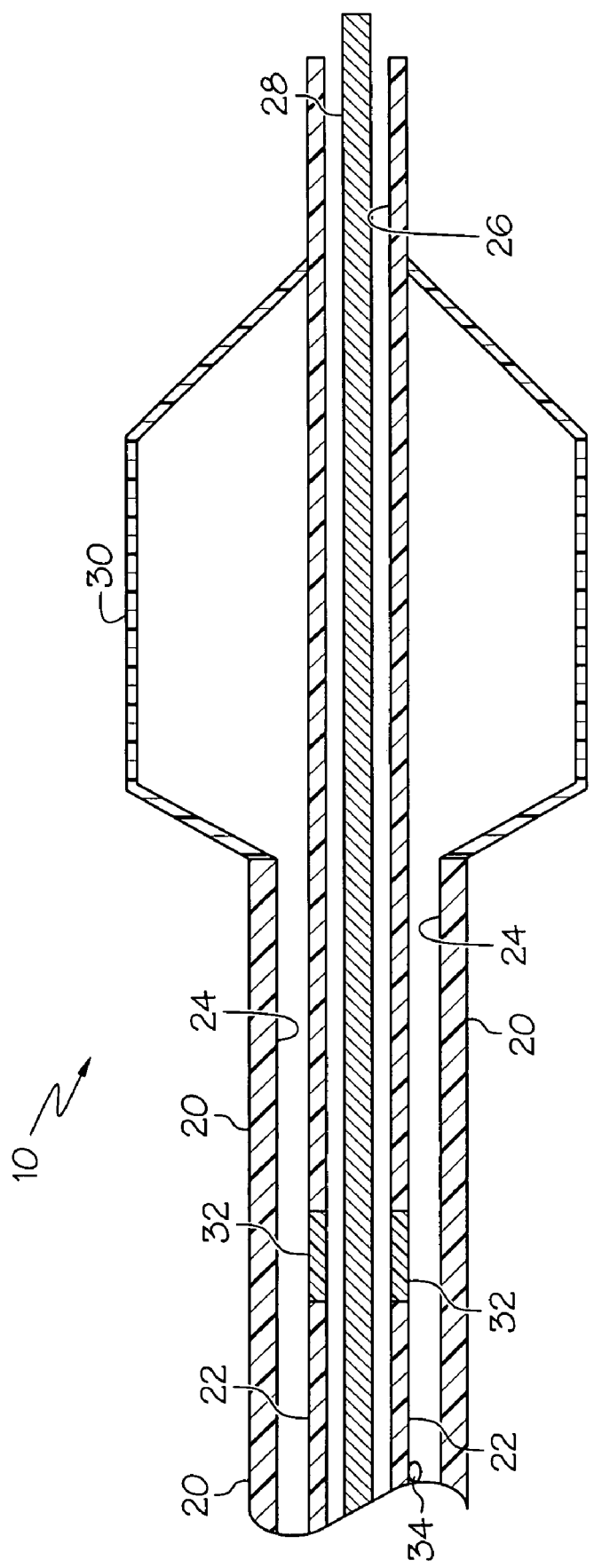
FIG. 5 is a longitudinal cross section of an embodiment where the inner shaft has a circumferential band of EAP.

In yet another embodiment, shown in FIG. 5, the inner shaft 22 has a circumferential section of EAP 32. In this embodiment, the circumferential section of EAP 32, in a non-actuated state, forms a section of the wall of the inner shaft 22. Thus, the exterior surface of the section of EAP 32 is substantially flush with the exterior surface of the inner shaft 22. Similarly, the interior surface of the EAP 32 is substantially flush with the interior surface of the inner shaft 22. However, in at least one embodiment, the section of EAP 32 may form only a portion of the wall of the inner shaft 22, i.e. the section of EAP 32 does not have the same thickness as the wall of the inner shaft 22. When the section of EAP 32 is in an actuated state, the section of EAP 32 engages the outer shaft 20 and blocks the inflation lumen 24. Thus, the diameter of the inflation lumen 24 is reduced to zero when the section of EAP 32 is in an actuated state. In at least one embodiment, the diameter of the inflation lumen 24 is reduced when the section of EAP 32 is in an actuated state but greater than zero. This embodiment can be used to control the flow of drugs or other beneficial agents through the inflation lumen 24 to the treatment site. In this embodiment, the non-actuated thickness of the wall of the inner shaft 22 is smaller than the actuated thickness of the wall of the inner shaft 22, thus, the outer diameter of the inner shaft 22 is smaller in a non-actuated state than in an actuated state. In addition, the non-actuated diameter of the catheter assembly 10 is substantially the same as the actuated diameter of the catheter assembly 10.

In another embodiment of the invention, shown in FIGS. 6a and 6b, the inner shaft 22 has one circumferential section of EAP 32 that bends when in an actuated state. FIG. 6b depicts that the section of EAP 32 has sufficient longitudinal length so that when the section of EAP 32 is in an actuated state, it engages the inner surface of the outer shaft 20 and blocks the inflation lumen 24. Thus, the section of EAP 32 causes the diameter of the inflation lumen 24 to be reduced. In at least one embodiment, the diameter of the inflation lumen 24 is equal to zero. In at least one embodiment, the diameter of the inflation lumen 24 is reduced when the section of EAP 32 is in an actuated state but it is greater than zero. This embodiment can be used to control the flow of drugs or other beneficial agents through the inflation lumen 24 to the treatment site.

In this embodiment, the exterior surface of the section of EAP 32 is substantially flush with the exterior surface of the inner shaft 22 in a non-actuated state but the interior surface of the section of EAP 32 is not flush with the interior surface of the inner shaft 22 since the section of EAP 32 is not as thick as the wall of the inner shaft 22. In this embodiment, the non-actuated thickness of the wall of the inner shaft 22 is larger than the actuated thickness of the wall of the inner shaft 22, thus, the outer diameter of the inner shaft 22 is larger in a non-actuated state than in an actuated state. In addition, the non-actuated diameter of the catheter assembly 10 is substantially the same as the actuated diameter of the catheter assembly 10.

In one embodiment, the circumferential section of EAP 32 is engaged to the exterior surface of the wall of the inner shaft 22. In at least one embodiment, the inner shaft 22 has a plurality of sections of EAP 32 that bend when in an actuated state. In this embodiment, the plurality of sections of EAP 32 changes the diameter of the inflation lumen 24 when in an actuated state. In at least one embodiment, the outer shaft 20 of a balloon catheter has at least one circumferential section of EAP 32 that bends when in an actuated state and engages the inner shaft 22. In this embodiment, the plurality of sections of EAP 32 changes the diameter of the inflation lumen 24 when in an actuated state. In at least one embodiment, the plurality of sections of EAP 32 increases the diameter of the inflation lumen 24 when in an acutated state. In at least one embodiment, the plurality of sections of EAP 32 reduces the diameter of the inflation lumen 24 when in an actuated state. In at least one embodiment, the plurality of sections of EAP 32 reduces the diameter of the inflation lumen 24 to zero when in an actuated state. Desirably, this embodiment is used for non-surgical Percutaneous Transluminal Septal Myocardial Ablation (PTSMA) using alcohol ablation.

In one embodiment, the guide wire 28 has at least one circumferential section of EAP 32 that bends when in an actuated state. In this embodiment, the section of EAP 32 changes the diameter of the guide wire lumen 26. In at least one embodiment, when the section of EAP 32 is in an actuated state the diameter of the guide wire lumen 26 increases. In at least one embodiment, when the section of EAP 32 is in an actuated state the diameter of the guide wire lumen is reduced. In at least one embodiment, when the section of EAP 32 is in an actuated state the diameter of the guide wire lumen 26 is equal to zero. Desirably, this embodiment is used for embolic protection.

FIG. 7 shows a portion of a generic balloon catheter 60. The balloon catheter 60 has an outer shaft 20, and inner shaft 22 and a guide wire 28. The outer shaft 20 has an interior surface that defines an inflation lumen 24. The inner shaft 22 has an interior surface that defines a guide wire lumen 26.

FIG. 8 is a cross-section of the generic balloon catheter 60 in FIG. 7 along line 7-7 where the balloon catheter 60 is modified by the addition of EAP 32 according to this embodiment. In this embodiment, the section of EAP 32 is in the form of a strip and the inner shaft 22 has three strips of EAP 32 embedded within the body of the inner shaft 22. The three strips of EAP 32 are disposed about the circumference of the inner shaft 22 at one position along the longitudinal length of the inner shaft 22. The strips of EAP 32 act as shaped actuatable support members. The counter-electrode 34 is engaged to the outer shaft 20. When the strips of EAP 32 are in an actuated state, the strips of EAP 32 can act like a lock or a buckle preventative. Because the catheter assembly 60 is less flexible when the strips of EAP 32 are in an actuated state due to an increase in rigidity, improve push is achieved. In this embodiment, the inner can move and sway to one side. In this embodiment, the non-actuated thickness of the wall of the inner shaft 22 is smaller than the actuated thickness of the wall of the inner shaft 22, thus the outer diameter of the inner shaft 22 is smaller in a non-actuated state than in an actuated state. In addition, the non-actuated diameter of the catheter assembly 60 is substantially the same as the actuated diameter of the catheter assembly 60.

In at least one embodiment, the inner shaft 22 has a plurality of strips of EAP 32 disposed about the circumference of the inner shaft 22 at a plurality of positions along the longitudinal length of the inner shaft 22. In at least one embodiment, the exterior surface of the three strips of EAP 32 are substantially flush with the exterior surface of the inner shaft 22 and the interior surface of the three strips of EAP 32 are substantially flush with the interior surface of the inner shaft 22. In one embodiment, the exterior surface of the three strips of EAP 32 are substantially flush with the exterior surface of the inner shaft 22 and the interior surface of the three strips of EAP 32 are not substantially flush with the interior surface of the inner shaft 22. In one embodiment, the exterior surface of the three strips of EAP 32 are not substantially flush with the exterior surface of the inner shaft 22 and the interior surface of the three strips of EAP 32 are substantially flush with the interior surface of the inner shaft 22. The length and width of the strip of EAP 32 can vary. The number of strips of EAP 32, the desired placement of the strips of EAP 32 and the circumference of the catheter shaft 22 affect the length of the strips of EAP 32.

The strip of EAP 32 does not have to be linear but can have different shapes. For example, in another embodiment, shown in FIG. 9a-d, the strip of EAP 32 is shaped into a coil and is located within the inflation lumen 24. FIG. 9a shows a longitudinal cross-section of the catheter assembly 60 with the coil of EAP 32 in a non-actuated state. The catheter assembly

60 consists of an outer shaft 20 which has a counter electrode 34 and is engaged to a balloon 30. The outer shaft 20 defines an inflation lumen 24. The coil of EAP 32 in this embodiment coils around the outer surface of the inner shaft 22. In one embodiment, the coil of EAP 32 forms a part of the wall of the inner shaft 22.

In this embodiment, the EAP 32 reinforces the inflation lumen 24 by providing extra strength to the outer shaft 20 when the EAP 32 is in an actuated state. FIG. 9*b* shows a longitudinal cross-section of the catheter assembly 60 with the coil of EAP 32 in an actuated state. FIG. 9*c* is a cross-section of the catheter assembly 60 in FIG. 9*b* taken at line 9-9. When the coil of EAP 32 is in an expanded state, a substantial portion of the coil of EAP 32 is engaged to the inner surface of the outer shaft 20 and no part of the coil of EAP 32 is engaged to the outer surface of the inner shaft 22. Thus, in this embodiment, the non-actuated thickness of the wall of the inner shaft 22 is larger than the actuated thickness of the wall of the inner shaft 22, thus, the outer diameter of the inner shaft 22 is larger in a non-actuated state than in an actuated state. In addition, the non-actuated diameter of the catheter assembly 60 is substantially the same as the actuated diameter of the catheter assembly 60. FIG. 9*d* shows a cross-section of an alternative design of the coil of EAP 32. In this embodiment, portions of the coil of EAP 32 are engaged with the inner surface of the outer shaft 20 and portions of the coil of EAP 32 are engaged with the outer surface of the inner shaft 22.

In at least one embodiment, the coil of EAP 32 forms a part of the interior surface of the outer shaft 20. In this embodiment, the actuation of the coil of EAP 32 causes the outer shaft 20 to expand, thereby increasing the diameter of the inflation lumen 24. In this embodiment, the non-actuated inner diameter of the outer shaft 20 is smaller than the actuated inner diameter of the outer shaft 20. The increased diameter of the inflation lumen 24 can increase fluid flow from the balloon 30, thereby decreasing the time it takes for the balloon 30 to deflate. In one embodiment, the coil of EAP 32 is engaged to a portion of the interior surface of the outer shaft 20.

FIG. 10 is a cross-section of the generic balloon catheter 60 in FIG. 7 along line 8-8 where the catheter 60 is modified by the addition of EAP 32 according to this embodiment. In this embodiment, the section of EAP 32 is a layer that forms the exterior surface of a portion of the outer shaft 20. The layer of EAP 32 can form the entire exterior surface layer of the outer shaft 20 or only a particular section or section(s) of the outer shaft 20 can have a layer of EAP 32.

For example, in at least one embodiment (not shown), only the exterior surface of the distal end region of the outer shaft 20 has a layer of EAP 32. When the physician is having trouble advancing the catheter 60 through the tortuous body lumen, the layer of EAP 32 can be actuated so that it will expand and provide improved track. After the difficult portion of the body lumen is traversed, the EAP 32 can be de-actuated and the initial profile obtained once again. In this embodiment, the non-actuated thickness of the wall of the outer shaft 20 is smaller than the actuated thickness of the wall of the outer shaft 20 and the non-actuated outer diameter of the outer shaft 20 is smaller than the actuated diameter of the outer shaft 20.

In one embodiment, the inner shaft 22 has a layer of EAP 32 on the inner surface. When activated, the layer of EAP 32 releases a lubricant into the guide wire lumen 26. Desirably, this improves the movement of the guide wire 28. Lubricants that may be released include but are not limited to hydrophilic polyacrylamides, fluoropolymers, silicone coatings such as MICROGLIDE or HYDROCOAT. In a non-actuated state the lubricant is partially surrounded by the EAP (the EAP forms a pocket like region that contains the lubricant). In an actuated state the volumetric increase of the EAP 32 causes the lubricant to be released from pocket like region. In at least one embodiment, either the outer shaft 20, the balloon 30, or both the outer shaft 20 and the balloon 30 has a layer of EAP 32 on the outer surface which releases a lubricant when actuated so that the track of the catheter is improved in difficult portions of the anatomy. In at least one embodiment, either the outer shaft 20, the balloon 30, or both the outer shaft 20 and the balloon 30 has a layer of EAP 32 on the outer surface which releases a drug when actuated.

In at least one embodiment (not shown), the inner shaft 22 has a layer of EAP 32 on the inner surface of the inner shaft 22. When the layer of EAP 32 is actuated, the guide wire lumen 26 increases in size, desirably this improves guide wire 28 movement. When the catheter assembly is in the proper position, the layer of EAP 32 can be de-actuated. In one embodiment, actuation of the layer of EAP 32 decreases the size of the inflation lumen 24. In this embodiment, de-actuation of the layer of EAP 32 will help inflation and deflation of the balloon 30 because the inflation lumen 24 is larger when the layer of EAP 32 is in a non-actuated state.

In another embodiment, shown in FIGS. 11*a-c*, both the outer shaft 20 and the inner shaft 22 have a layer of EAP 32. FIG. 11*b* is an expanded view of a portion of the catheter assembly 10 in FIG. 11*a*. The EAP 32 in the outer shaft 20 volumetrically contracts or retracts when it is in the actuated state. Therefore, the non-actuated thickness of the wall of the outer shaft 20 is larger than the actuated thickness of the wall of the outer shaft 20, thus the non-actuated inner diameter of the outer shaft 20 is smaller than the actuated inner diameter of the outer shaft 20. The EAP 32 in the inner shaft 22 volumetrically contracts when in an actuated state. Therefore, the non-actuated thickness of the wall of the inner shaft 22 is larger than the actuated thickness of the inner shaft 22, thus, the non-actuated outer diameter of the inner shaft 22 is larger than the actuated diameter of the inner shaft 22. In combination, when in an actuated state, the two layers of EAP 32 cause the diameter of the inflation lumen 24 to enlarge, which increases fluid flow from the balloon 30, thereby decreasing the deflation time. This is shown in FIG. 11*c*.

FIGS. 12*a* and 12*b* illustrate the distal end region of a balloon catheter 60 with only one lumen. The balloon catheter 60 has a shaft 50, a balloon 30, a guide wire 28 and at least two sections of EAP 32. The guide wire 28 extends along the exterior of the shaft 50 until the distal end region where the guide wire 28 enters into the inflation lumen 24 of the balloon catheter 60 through a guide wire opening 62 in the wall of the shaft 50 and extends distally through the inflation lumen 24 past the distal end of the balloon catheter 60.

There is a section of EAP 32*a* that surrounds the guide wire opening 62 and a circumferential band of EAP 32*b* positioned at the distal tip 64 of the shaft 50. In FIG. 12*a*, the sections of EAP 32 are in a non-actuated state, while in FIG. 12*b* the sections of EAP 32 are in an actuated state. Note that when the circumferential band of EAP 32*b* positioned at the distal tip 64 is in an actuated state, the diameter of the inflation lumen 24 decreases. In at least one embodiment, when the circumferential band of EAP 32*b* at the distal tip 64 is in an actuated state, the diameter of the inflation lumen 24 is equal to zero.

FIGS. 12*c* and 12*d* show a portion of the side of the balloon catheter 60 to illustrate the section of EAP 32 surrounding the guide wire opening 62 in a non-actuated state (FIG. 12*c*) and in an actuated state (FIG. 12*d*). In FIGS. 12*c* and 12*d*, the section of EAP 32 surrounding the opening is substantially round but the section of EAP 32 can have any shape so long as when the EAP 32 is in an actuated state the guide wire opening 62 becomes occluded to allow for the inflation of the balloon 30. In order to occlude the guide wire opening 62, the section of EAP 32 may increase in length towards the guide wire 28 or the section of EAP 32 may volumetrically increase in size. Either way the EAP 32 will engage the guide wire 28 and occlude the guide wire opening 62.

In use, the sections of EAP 32 would be in a non-actuated state while the balloon catheter 60 is being maneuvered through the vasculature. Then, when the balloon catheter 60 is in the desired position within the vasculature, the sections of EAP 32 would be actuated so that the balloon 30 can be inflated. Thus, actuation of the sections of EAP provides a seal against the guide wire 28 at both the guide wire opening 62 and the distal tip 64 and allows the catheter to pressurize without the need for separate lumens for the guide wire 28 and inflation. Desirably, the elimination of separate lumens allows for reduced system complexity and lower catheter profiles.

Note that it is within the scope of the invention for the embodiments that increase the diameter of the shaft but do not affect the diameter of the lumen, for example, the embodiments illustrated in FIGS. 2a-c, 2g-h, 2i-j, 2k-l, 4 and 10 to be combined with the embodiments that affect the diameter of a catheter lumen, for example, the embodiments illustrated in FIGS. 2d, 2e, 2f, 3a-d, 5, 6a-6b, 9a-9d, 11a-11c, 12a-d. Thus, in at least one embodiment, the catheter has at least one section of EAP 32 that affects the diameter of at least one catheter shaft and at least one section of EAP 32 that affects the diameter of at least one catheter lumen. In at least one embodiment, the catheter has at least one section of EAP 32 that affects the diameter of at least one shaft of the catheter and at least one section of EAP 32 that affects both the diameter of at least one catheter shaft and at least one catheter lumen. In at least one embodiment, the catheter has at least one section of EAP 32 that engages the catheter to the vessel when in an actuated state and at least one section of EAP 32 that changes the diameter of at least one catheter lumen when in an actuated state.

One means to actuate the section(s) of EAP in the embodiments described above is to introduce a charged inflation media into the inflation lumen of the catheter assembly.

The invention also includes the following embodiments as characterized in the following numbered statements:

1. A catheter comprising a catheter shaft with a lumen therethrough, at least a portion of the catheter shaft including an electroactive polymer, wherein upon actuation or deactuation of the electroactive polymer, a cross-sectional area of the lumen changes in size.

2. The catheter of statement 1 wherein upon actuation of the electroactive polymer, a diameter of the lumen in the vicinity of the electroactive polymer decreases.

3. The catheter of statement 1 wherein the electroactive polymer forms a plug in the lumen when unactuated.

4. The catheter of statement 3 wherein the electroactive polymer is located proximal to a balloon disposed about the catheter shaft.

5. The catheter of statement 4 wherein the electroactive polymer upon actuation ceases to plug the catheter shaft.

6. The catheter of statement 1, the electroactive polymer forming an outer surface of a portion of the catheter shaft, wherein on actuation of the electroactive polymer, an outer diameter of the catheter shaft in the vicinity of the electroactive polymer increases.

7. The catheter of statement 6 wherein the outer diameter of the catheter shaft increases by more than 20% on actuation of the electroactive polymer.

8. The catheter of statement 1 wherein the electroactive polymer comprises a therapeutic agent or lubricant.

9. The catheter of statement 1 wherein the therapeutic agent or lubricant is released by actuation of the electroactive polymer.

10. The catheter of statement 1 wherein the electroactive polymer is configured to form a valve extending within the lumen.

11. The catheter of statement 10 wherein the valve may be opened by actuation of the electroactive polymer.

12. The catheter of statement 10 wherein the valve may be closed by actuation of the electroactive polymer.

13. The catheter of statement 1 wherein the electroactive polymer forms an interior surface of at least a portion of the catheter shaft and an exterior surface of at least a portion of the catheter shaft.

14. The catheter of statement 13 wherein an outer diameter of the catheter shaft in the vicinity of the electroactive polymer increases upon actuation or deactuation of the electroactive polymer.

15. The catheter of statement 13 wherein an outer diameter of the catheter shaft in the vicinity of the electroactive polymer decreases upon actuation or deactuation of the electroactive polymer.

16. The catheter of statement 13 wherein an inner diameter of the catheter shaft in the vicinity of the electroactive polymer increases upon actuation or deactuation of the electroactive polymer.

17. The catheter of statement 13 wherein an inner diameter of the catheter shaft in the vicinity of the electroactive polymer decreases upon actuation or deactuation of the electroactive polymer.

18. The catheter system of statement 1 wherein the electroactive polymer upon actuation is configured to at least partially constrict the lumen.

19. The catheter of statement 1 wherein the electroactive polymer is in the form of a coil.

20. The catheter system of statement 19 wherein the coil forms a portion of an outer surface of the electroactive catheter shaft.

21. The catheter system of statement 19 wherein the coil forms a portion of an inner surface of the electroactive catheter shaft.

22. The catheter system of statement 1 further comprising a catheter shaft which is not electroactive.

23. The catheter system of statement 1 comprising a plurality of the electroactive catheter shaft.

24. The catheter system of statement 1 further comprising a control mechanism in communication with the electroactive catheter shaft to allow for selective actuation and deactuation of the electractive polymer.

25. A balloon catheter system comprising a balloon disposed about a catheter and an inflation lumen, the inflation lumen in fluid communication with the balloon, the inflation lumen including an electroactive polymer which may be actuated or deactuated to control the flow of an inflation fluid to the balloon.

25. The balloon catheter of statement 25 wherein the electroactive polymer expands inward into the inflation lumen upon actuation.

26. A catheter comprising a first catheter shaft and at least one section of electroactive polymer, the first catheter shaft comprising a wall, the wall of the first catheter shaft having a thickness and defining a first lumen, the first lumen having a diameter, the at least one section of electroactive polymer comprising at least one first electroactive polymer, the at least one first electroactive polymer having a non-actuated state and an actuated state, the at least one first electroactive polymer in the actuated state causing the thickness of the wall of the first catheter shaft to change and causing the diameter of the first lumen to change.

27. The catheter of statement 26, the at least one section of electroactive polymer further comprising at least one second electroactive polymer, the at least one second electroactive polymer having a non-actuated state and an actuated state, the at least one second electroactive polymer in the actuated state causing the thickness of the wall of the first catheter shaft to change, the diameter of the first lumen remaining substantially the same diameter.

28. The catheter of statement 27, further comprising a second catheter shaft, the second catheter shaft comprising at least one section of electroactive polymer, the second catheter shaft having a wall, the at least one section of electroactive polymer comprising at least one third electroactive polymer, the at least one third electroactive polymer having a non-actuated state and an actuated state, the wall of the second catheter shaft having a thickness and defining a second lumen, the second lumen having a diameter, the at least one third electroactive polymer in the actuated state causing the thickness of the wall of the second catheter shaft and the diameter of the second lumen to change.

29. The catheter of statement 28, that least one section of electroactive polymer comprising at least one fourth electroactive polymer, the at least one fourth electroactive polymer having a non-actuated state and an actuated state, the at least one fourth electroactive polymer, in the actuated state causing the thickness of the wall of the second catheter shaft to change, the diameter of the second lumen remaining substantially the same diameter.

30. A catheter comprising a first catheter, a second catheter and at least one section of electroactive polymer, the second catheter positioned about the first catheter, the second catheter comprising a wall, the wall of the second catheter having a thickness and defining a second lumen, the second lumen having a diameter, the at least one section of electroactive polymer comprising at least one third electroactive polymer, the at least one third electroactive polymer having an actuated state, the at least one third electroactive polymer in the actuated state causing the thickness of the wall of the second catheter shaft to change and causing the diameter of the second lumen to change.

31. The catheter of statement 30, the at least one section of electroactive polymer forming a portion of the wall of the second catheter shaft.

32. The catheter of statement 30, the at least one section of electroactive polymer engaged to the wall of the second catheter shaft.

33. The catheter of statement 30, the at least one third electroactive polymer in the actuated state causing the second lumen to have a diameter equal to zero.

34. The catheter of statement 30, the at least one third electroactive polymer bending when actuated.

35. The catheter of statement 34, the at least one third electroactive polymer engaging the second catheter shaft to the first catheter shaft when in an actuated state.

36. The catheter of statement 30, the first catheter shaft comprising a wall, the at least one section of electroactive polymer further comprising at least one second electroactive polymer, the at least one second electroactive polymer forming an outer surface layer of the wall of the first catheter shaft, the at least one third electroactive polymer forming an inner surface layer of the wall of the second catheter shaft, and actuation of at least one of the layers of electroactive polymer causing the diameter of the second lumen to change.

37. The catheter of statement 36 further comprising a balloon.

38. The catheter of statement 30, the at least one third electroactive polymer forming a coil engaged to the wall of the second catheter shaft.

39. The catheter of statement 38, the at least one third electroactive polymer in an actuated state causing the diameter of the second lumen to change.

40. The catheter of statement 30, wherein the second catheter shaft is a guide catheter, actuation of the third electroactive polymer engages the guide catheter to the first catheter shaft.

41. The catheter of statement 30, that least one section of electroactive polymer further comprising at least one fourth electroactive polymer, the at least one fourth electroactive polymer having an actuated state, the at least one fourth electroactive polymer, in the actuated state causing the thickness of the wall of the second catheter shaft to change, the diameter of the second lumen remaining substantially the same diameter.

42. The catheter of statement 41, wherein the at least one fourth electroactive polymer is selected from at least one member of the group consisting of a circumferential band, a longitudinal strip, a spot, a spiral band, a layer and any combination thereof.

43. The catheter of statement 42, wherein actuation of the at least one fourth electroactive polymer engages the second catheter shaft to a wall defining a body lumen.

44. The catheter of statement 41, the catheter further comprising a balloon, the at least one fourth electroactive polymer a circumferential band located proximal to the balloon.

45. The catheter of statement 41, the at least one fourth electroactive polymer forming two circumferential bands longitudinally separated from one another, the wall of the second catheter shaft having at least two perforations between the two circumferential bands.

The shafts of the catheters of the present invention are manufactured from any suitable material to impart the desired characteristics and EAPs. Examples of suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro (propyl vinyl ether) (PFA), polyether-ester, polymer/metal composites, etc., or mixtures, blends or combinations thereof. One example of a suitable polyether block ester is available under the trade name ARNITEL, and one suitable example of a polyether block amide (PEBA) is available under the trade name PEBAX®, from ATOMCHEM POLYMERS, Birdsboro, Pa.

The catheters of the present invention are actuated, at least in part, using EAP actuators. EAPs are characterized by their ability to change shape in response to electrical stimulation. EAPs include electric EAPs and ionic EAPs. Piezoelectric materials may also be employed, but tend to undergo small deformation when voltage is applied.

Electric EAPs include ferroelectric polymers, dielectric EAPs, electrorestrictive polymers such as the electrorestrictive graft elastomers and electro-viscoelastic elastomers, and liquid crystal elastomer materials.

Ionic EAPs include ionic polymer gels, ionomeric polymer-metal composites, conductive polymers and carbon nanotubes. Upon application of a small voltage, ionic EAPs can bend significantly. Ionic EAPs also have a number of additional properties that make them attractive for use in the devices of the present invention, including the following: (a) they are lightweight, flexible, small and easily manufactured; (b) energy sources are available which are easy to control, and energy can be easily delivered to the EAPs; (c) small changes in potential (e.g., potential changes on the order of 1V) can be used to effect volume change in the EAPs; (d) they are relatively fast in actuation (e.g., full expansion/contraction in a few seconds); (e) EAP regions can be created using a variety of techniques, for example, electrodeposition; and (f) EAP regions can be patterned, for example, using photolithography, if desired.

Conductive plastics may also be employed. Conductive plastics include common polymer materials which are almost exclusively thermoplastics that require the addition of conductive fillers such as powdered metals or carbon (usually carbon black or fiber).

Ionic polymer gels are activated by chemical reactions and can become swollen upon a change from an acid to an alkaline environment.

Ionomeric polymer-metal composites can bend as a result of the mobility of cations in the polymer network. Suitable base polymers include perfluorosulfonate and perfluorocarboxylate.

Essentially any EAP that exhibits contractile or expansile properties may be used in connection with the various active regions of the invention, including any of those listed above.

In some embodiments herein, the EAPs employed are ionic EAPs, more specifically, the ionic EAPs are conductive polymers that feature a conjugated backbone (they include a backbone that has an alternating series of single and double carbon-carbon bonds, and sometimes carbon-nitrogen bonds, i.e. π-conjugation) and have the ability to increase the electrical conductivity under oxidation or reduction. For polymers, this allows freedom of movement of electrons, therefore allowing the polymers to become conductive. The pi-conjugated polymers are converted into electrically conducting materials by oxidation (p-doping) or reduction (n-doping).

The volume of these polymers changes dramatically through redox reactions at corresponding electrodes through exchanges of ions with an electrolyte. The EAP-containing active region contracts or expands in response to the flow of ions out of, or into, the same. These exchanges occur with small applied voltages and voltage variation can be used to control actuation speeds.

Any of a variety of pi-conjugated polymers may be employed herein. Examples of suitable conductive polymers include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyanthraquinones, poly(N-vinylcarbazole)s and polyacetylenes, with the most common being polythiophenes, polyanilines, and polypyrroles.

Some of the structures are shown below:

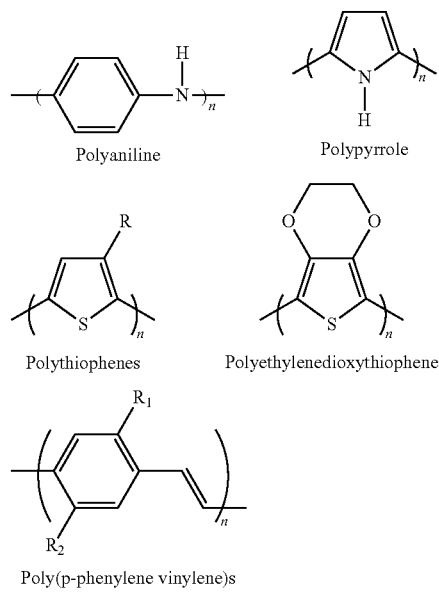

Polyaniline  Polypyrrole

Polythiophenes  Polyethylenedioxythiophene

Poly(p-phenylene vinylene)s

Polypyrrole, shown in more detail below, is one of the most stable of these polymers under physiological conditions:

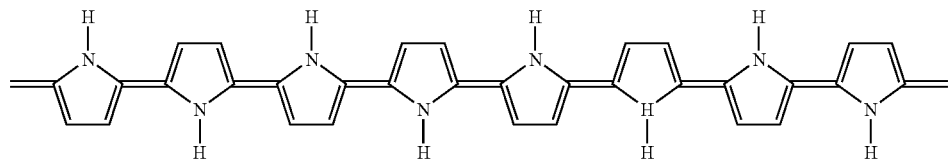

The above list is intended for illustrative purposes only, and not as a limitation on the scope of the present invention.

The behavior of conjugated polymers is dramatically altered with the addition of charge transfer agents (dopants). These materials can be oxidized to a p-type doped material by doping with an anionic dopant species or reducible to an n-type doped material by doping with a cationic dopant species. Generally, polymers such as polypyrrole (PPy) are partially oxidized to produce p-doped materials:

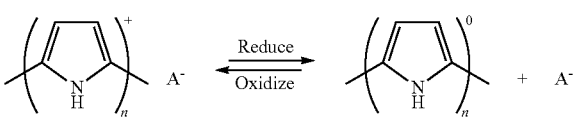

Dopants have an effect on this oxidation-reduction scenario and convert semi-conducting polymers to conducting versions close to metallic conductivity in many instances. Such oxidation and reduction are believed to lead to a charge imbalance that, in turn, results in a flow of ions into or out of the material. These ions typically enter/exit the material from/into an ionically conductive electrolyte medium associated with the EAP.

Dimensional or volumetric changes can be effectuated in certain polymers by the mass transfer of ions into or out of the polymer. This ion transfer is used to build conductive polymer actuators (volume change). For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 10%). These characteristics are ideal for construction of the devices of the present invention. As used herein, the expansion or the contraction of the active region of the device is generally referred to as "actuation."

The following elements are commonly utilized to bring about EAP actuation: (a) a source of electrical potential, (b) an active region, which comprises the EAP, (c) a counter electrode and (d) an electrolyte in contact with both the active region and the counter electrode.

The source of electrical potential for use in connection with the present invention can be quite simple, consisting, for example, of a dc battery and an on/off switch. Alternatively, more complex systems can be utilized. For example, an electrical link can be established with a microprocessor, allowing a complex set of control signals to be sent to the EAP-containing active region(s).

The electrolyte, which is in contact with at least a portion of the surface of the active region, allows for the flow of ions and thus acts as a source/sink for the ions. Any suitable electrolyte may be employed herein. The electrolyte may be, for example, a liquid, a gel, or a solid, so long as ion movement is permitted. Examples of suitable liquid electrolytes include, but are not limited to, an aqueous solution containing a salt, for example, a NaCl solution, a KCl solution, a sodium dodecylbenzene sulfonate solution, a phosphate buffered solution, physiological fluid, etc. Examples of suitable gel electrolytes include, but are not limited to, a salt-containing agar gel or polymethylmethacrylate (PMMA) gel. Solid electrolytes include ionic polymers different from the EAP and salt films.

The counter electrode may be formed from any suitable electrical conductor, for example, a conducting polymer, a conducting gel, or a metal, such as stainless steel, gold or platinum. At least a portion of the surface of the counter electrode is generally in contact with the electrolyte, in order to provide a return path for charge.

In one specific embodiment, the EAP employed is polypyrrole. Polypyrrole-containing active regions can be fabricated using a number of known techniques, for example, extrusion, casting, dip coating, spin coating, or electro-polymerization/deposition techniques. Such active regions can also be patterned, for example, using lithographic techniques, if desired.

As a specific example of a fabrication technique, polypyrrole can be galvanostatically deposited on a platinised substrate from a pyrrole monomer solution using the procedures described in D. Zhou et al., "Actuators for the Cochlear Implant," *Synthetic* Metals 135-136 (2003) 39-40. Polypyrrole can also be deposited on gold. In some embodiments, adhesion of the electrodeposited polypyrrole layer is enhanced by covering a metal such as gold with a chemisorbed layer of molecules that can be copolymerized into the polymer layer with chemical bonding. Thiol is one example of a head group for strong chemisorption to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

Various dopants, including large immobile anions and large immobile cations, can be used in the polypyrrole-containing active regions. According to one specific embodiment, the active region comprises polypyrrole (PPy) doped with dodecylbenzene sulfonate (DBS) anions. When placed in contact with an electrolyte containing small mobile cations, for example, $Na^+$ cations, and when a current is passed between the polypyrrole-containing active region and a counter electrode, the cations are inserted/removed upon reduction/oxidation of the polymer, leading to expansion/contraction of the same. This process can be represented by the following equation:

$$PPy^+(DBS^-) + Na^+ + e^- \leftrightarrow PPy^o(Na^+DBS^-)$$

where $Na^+$ represents a sodium ion, $e^-$ represents an electron, $PPy^+$ represents the oxidized state of the polypyrrole, $PPy^o$ represents the reduced state of the polymer, and species are enclosed in parentheses to indicate that they are incorporated into the polymer. In this case the sodium ions are supplied by the electrolyte that is in contact with the EAP member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer.

EAP-containing active regions can be provided that either expand or contract when an applied voltage of appropriate value is interrupted depending, for example, upon the selection of the EAP, dopant, and electrolyte.

Additional information regarding EAP actuators, their design considerations, and the materials and components that may be employed therein, can be found, for example, in E. W. H. Jager, E. Smela, O. Inganäs, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and *Proceedings of the SPIE*, Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

Furthermore, networks of conductive polymers may also be employed. For example, it has been known to polymerize pyrrole in EAP networks such as poly(vinylchloride), poly (vinyl alcohol), NAFION®, a perfluorinated polymer that contains small proportions of sulfonic or carboxylic ionic functional groups, available from E.I. DuPont Co., Inc. of Wilmington, Del.

EAPs are also discussed in detail in U.S. Patent Application Publications 2004/0143160 and 2004/0068161 and commonly assigned copending U.S. patent application Ser. No. 10/763,825, the entire content of which is incorporated by reference herein.

In some embodiments the catheter may include one or more areas, bands, coatings, members, etc. that is (are) detectable by imaging modalities such as X-Ray, MRI, ultrasound, etc. In some embodiments at least a portion of the catheter is at least partially radiopaque.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A catheter, the catheter comprising an inner shaft, an outer shaft, and a balloon, the inner shaft disposed within the outer shaft, the balloon engaged to the outer shaft, the outer shaft defining an inflation lumen in fluid communication with the balloon, the catheter further comprising a first electroactive polymer and a second electroactive polymer, each electroactive polymer having an actuated state and a non-actuated state, the first electroactive polymer forming an inner surface of the outer shaft, the second electroactive polymer forming an outer surface of the inner shaft, the inflation lumen having a first diameter when each of the first and second electroactive polymers is in the actuated state, the inflation lumen having a second diameter when each of the first and second electroactive polymers is in the non-actuated state, the first diameter being greater than the second diameter, each shaft having a thickness, the thickness of each shaft being greater when the electroactive polymer is in the non-actuated state than when the electroactive polymer is in the actuated state.

2. The catheter of claim 1 wherein the at least one section of electroactive polymer is an electric electroactive polymer or an ionic electroactive polymer.

3. The catheter of claim 2 wherein the at least one section of electroactive polymer is an ionic electroactive polymer selected from the group consisting of conductive polymers, ionic polymer gels, ionomeric polymer-metal composites, carbon nanotubes and mixtures thereof.

4. The catheter of claim 3 wherein the ionic electroactive polymer is a conductive polymer selected from the group consisting of polypyrroles, polyanilines, polythiophenes, polyethylenedioxythiophenes, poly(p-phenylene vinylene)s, polysulfones, polyacetylenes and mixtures thereof.

\* \* \* \* \*